US008885912B2

(12) United States Patent
Sui

(10) Patent No.: US 8,885,912 B2
(45) Date of Patent: Nov. 11, 2014

(54) GENERATE PERCENTAGE OF POSITIVE CELLS FOR BIOMARKERS BY NORMALIZING AND AUTOTHRESHOLDING THE IMAGE INTENSITY PRODUCED BY IMMUNOHISTOCHEMISTRY TECHNIQUE

(75) Inventor: Yunxia Sui, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 274 days.

(21) Appl. No.: 13/288,665

(22) Filed: Nov. 3, 2011

(65) Prior Publication Data

US 2013/0116511 A1    May 9, 2013

(51) Int. Cl.
*G06K 9/00* (2006.01)
*G06F 19/24* (2011.01)
*G06F 19/18* (2011.01)

(52) U.S. Cl.
CPC ............ *G06F 19/24* (2013.01); *G06K 9/00147* (2013.01); *G06F 19/18* (2013.01)
USPC ............................. 382/133; 382/134; 382/128

(58) Field of Classification Search
None
See application file for complete search history.

(56) References Cited

U.S. PATENT DOCUMENTS

| 7,200,251 | B2 * | 4/2007 | Joshi et al. ..................... 382/128 |
| 8,116,551 | B2 * | 2/2012 | Gallagher et al. ............ 382/133 |
| 2003/0156111 | A1 * | 8/2003 | Joshi et al. ..................... 345/420 |
| 2005/0163359 | A1 * | 7/2005 | Murao et al. ................... 382/128 |
| 2006/0072816 | A1 * | 4/2006 | Szajnowski et al. .......... 382/168 |
| 2006/0078926 | A1 * | 4/2006 | Marcelpoil et al. ................ 435/6 |
| 2007/0211928 | A1 * | 9/2007 | Weng et al. .................... 382/128 |
| 2008/0033657 | A1 | 2/2008 | Cline et al. |
| 2010/0177950 | A1 | 7/2010 | Donovan et al. |
| 2010/0254589 | A1 * | 10/2010 | Gallagher ..................... 382/133 |
| 2011/0091081 | A1 | 4/2011 | Sarachan et al. |
| 2011/0091091 | A1 | 4/2011 | Sarachan et al. |
| 2011/0110569 | A1 * | 5/2011 | Weng et al. .................... 382/128 |
| 2011/0182490 | A1 * | 7/2011 | Hoyt et al. ..................... 382/128 |
| 2013/0230221 | A1 * | 9/2013 | Bolstad et al. ................ 382/128 |

OTHER PUBLICATIONS

Francisco et al., "Evaluation of the Image-Pro Plus 4.5 Software for Automatic Counting of Labeled Nuclei by PCNA Immunohistochemistry", Oral Pathology, vol. 18, Issue 2, Jun. 2004.
Hatanaka et al., "Cytometrical Image Analysis for Immunohistochemical Hormone Receptor Status in Breast Carcinomas", Pathology International, vol. 53, Issue 10, pp. 693-699, Oct. 2003.

(Continued)

*Primary Examiner* — Avinash J Yentrapati
(74) *Attorney, Agent, or Firm* — Eileen B. Gallagher

(57) ABSTRACT

A computer implemented method of analyzing tissue features based on multiplexed biometric images includes storing a data set including cell profile data and an assessment associated with a field of view or a patient. The cell profile data includes biomarker expression intensity data for at least one cell feature. The method includes normalizing the biomarker expression intensity data for each field of view. The method includes determining a plurality of positive cell percentages for a first cell feature for each field of view or for each patient based on a plurality of normalized expression cutoffs for all fields of view. The method further includes correlating positive cell percentages with assessments for each field of view or each patient. The method also includes identifying a combination of a cell feature for expression of a biomarker and a normalized expression cutoff that most closely correlate the positive cell percentage with the assessment.

31 Claims, 14 Drawing Sheets

(56) References Cited

OTHER PUBLICATIONS

Idikio et al., "Quantitative Analysis of p53 Expression in Human Normal and Cancer Tissue Microarray with Global Normalization Method", International Journal of Clinical and Experimental Pathology, vol. 4, pp. 505-512, Jun. 20, 2011.

Lehr et al., "Quantitative Evaluation of HER-2/neu Status in Breast Cancer by Fluorescence in Situ Hybridization and by Immunohistochemistry with Image Analysis", American Journal of Clinical Pathology, vol. 115, pp. 814-822, Jun. 2001.

Nassar et al., "A New Immunohistochemical ER/PR Image Analysis System: A Multisite Performance Study", Applied Immunohistochemistry & Molecular Morphology, vol. 19, Issue 3, pp. 195-202, May 2011.

Tilley et al., "Detection of Discrete Androgen Receptor Epitopes in Prostate Cancer by Immunostaining: Measurement by Color Video Image Analysis", Cancer Research, vol. 54, pp. 4096-4102, Aug. 1, 1994.

Zlobec et al., "Selecting Immunohistochemical Cut-off Scores for Novel Biomarkers of Progression and Survival in Colorectal Cancer", Journal of Clinical Pathology, vol. 60, pp. 1112-1116, Oct. 2007.

Search Report and Written Opinion from corresponding PCT Application No. PCT/EP2812/871669 dated Jun. 24, 2013.

Silvestrini et al., "P53 and bcl-2 Expression Correlates With Clinical Outcome in a Series of Node-Positive Breast Cancer Patients", Journal of Clinical Oncology, vol. 14, No. 5, pp. 1604-1610, May 1996.

Cheang et al., "Ki67 Index, HER2 Status, and Prognosis of Patients With Luminal B Breast Cancer", Journal of the National Cancer Institute, vol. 101, No. 10, pp. 736-750, May 20, 2009.

\* cited by examiner

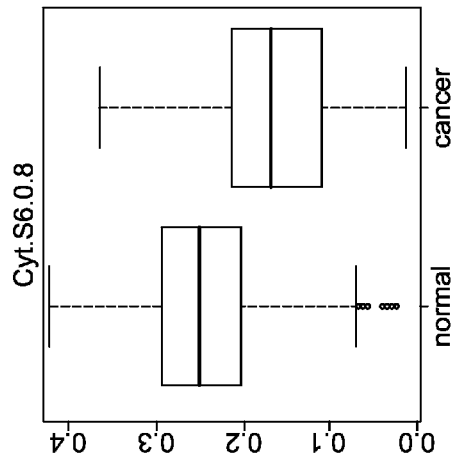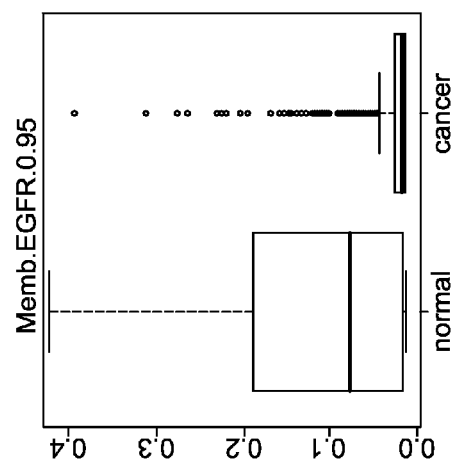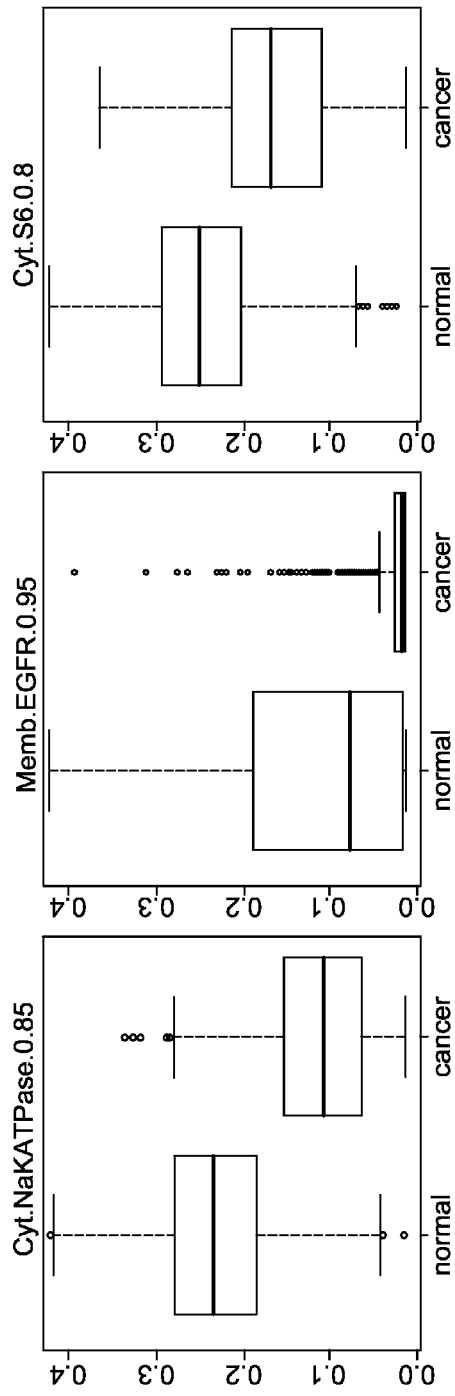
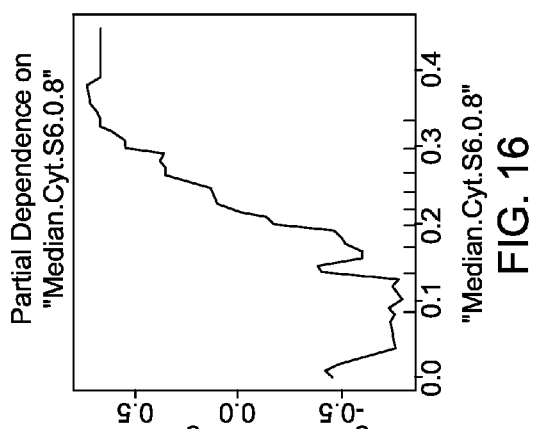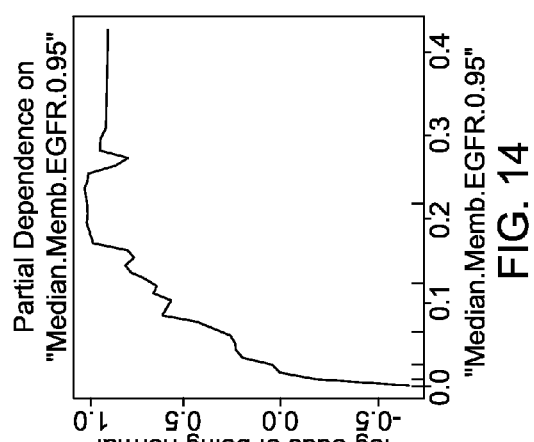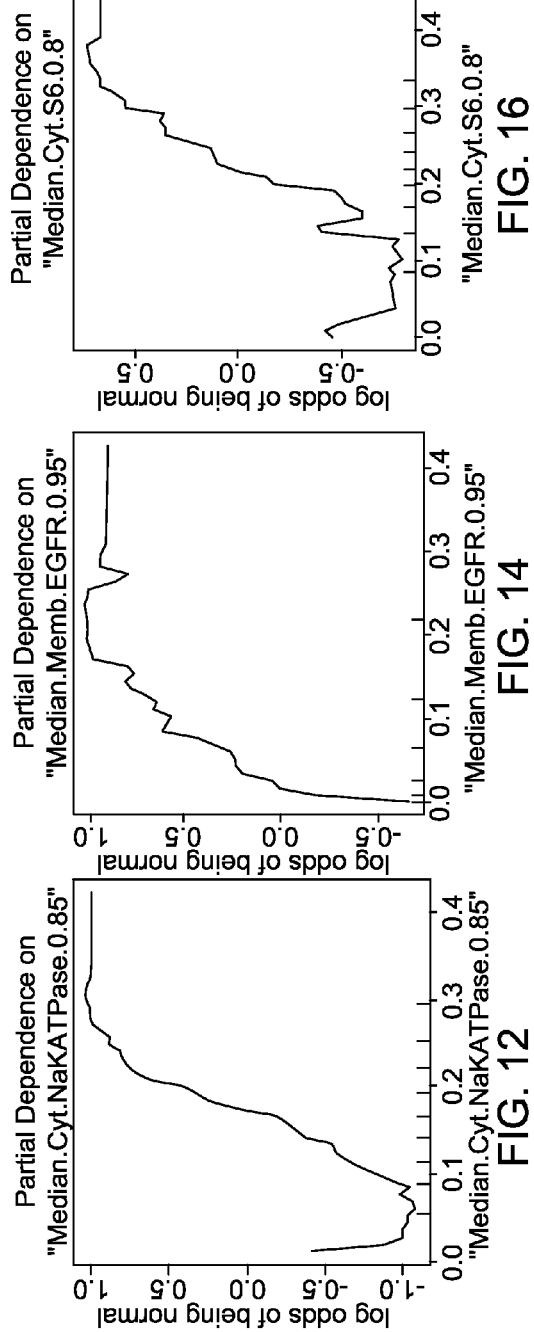
FIG. 11  FIG. 13  FIG. 15
FIG. 12  FIG. 14  FIG. 16

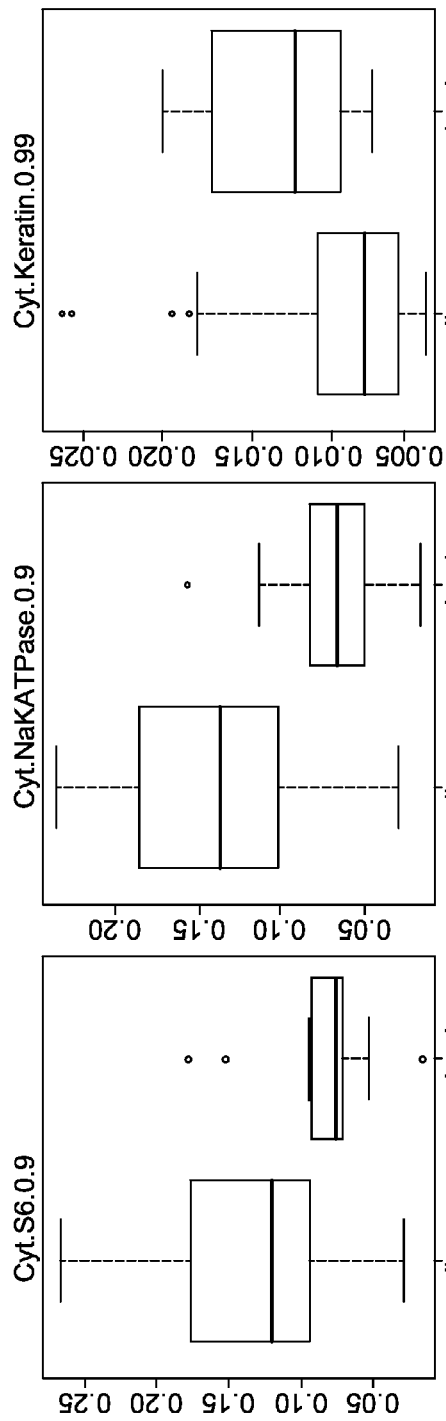
FIG. 20
FIG. 22
FIG. 24
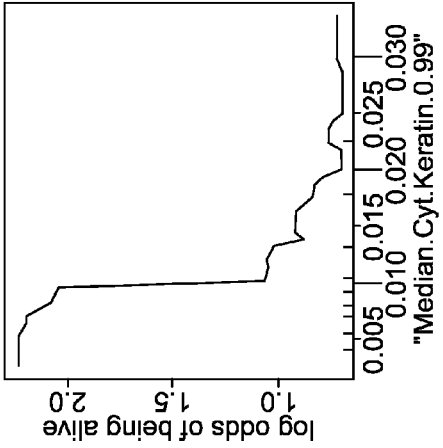
FIG. 25
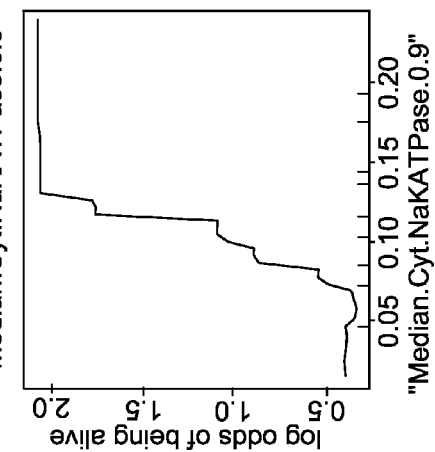
FIG. 23
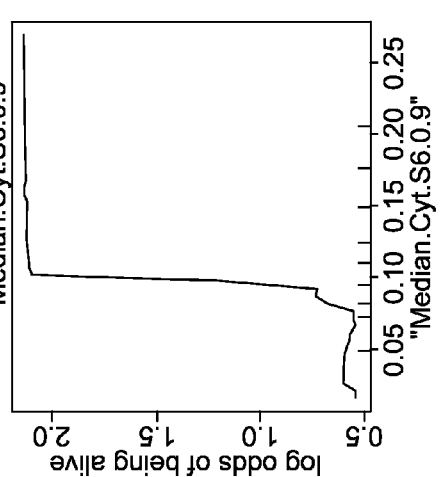
FIG. 21

GENERATE PERCENTAGE OF POSITIVE CELLS FOR BIOMARKERS BY NORMALIZING AND AUTOTHRESHOLDING THE IMAGE INTENSITY PRODUCED BY IMMUNOHISTOCHEMISTRY TECHNIQUE

FIELD

The embodiments relate generally to analyzing the expression of biomarkers in individual cells.

BACKGROUND

Examination of tissue specimens that have been treated to reveal the expression of biomarkers is a known tool for biological research and clinical studies. One such treatment involves the use of antibodies or antibody surrogates, such as antibody fragments, that are specific for the biomarkers, commonly proteins, of interest. Such antibodies or antibody surrogates can be directly or indirectly labeled with a moiety capable, under appropriate conditions, of generating a signal. For example, a fluorescent moiety can be attached to the antibody to interrogate the treated tissue for fluorescence. The signal obtained is commonly indicative of not only the presence but also the amount of biomarker present.

The techniques of tissue treatment and examination have been refined so that the level of expression of a given biomarker in a particular cell or even a compartment of the given cell such as the nucleus, cytoplasm or membrane can be quantitatively determined. The boundaries of these compartments or the cell as a whole are located using known histological stains. Commonly, the treated tissue is examined with digital imaging and the level of different signals emanating from different biomarkers can consequently be readily quantified.

A technique has further been developed which allows testing a given tissue specimen for the expression of numerous biomarkers. Generally this technique involves staining the specimen with a fluorophore labeled probe to generate signal for one or more probe-bound biomarkers, chemically bleaching these signals and re-staining the specimen to generate signals for some further biomarkers. The chemical bleaching step is convenient because there are only a limited number of signals that can be readily differentiated from each other so only a limited number of biomarkers can be examined in a particular step. But with bleaching, the sample may be re-probed and re-evaluated for multiple steps. This cycling method may be used on formalin fixed paraffin embedded tissue (FFPE) samples and cells. Another approach has been to examine frozen tissue specimens by staining them iteratively and photo bleaching the labels from the previous staining step before applying the next set of stains. The strength of the fluorescent signal associated with each biomarker evaluated is then extracted from the appropriate image.

In either approach, digital images of the specimen are collected after each staining step. The successive images of such a specimen can conveniently be kept in registry using morphological features such as DAPI stained cell nuclei, the signal of which is not modified by the chemical bleaching method. Different images (or image data) showing expression of different biomarkers by the same cells, which have been registered with each other based on morphological features, may be referred to multiplexed biometric images.

SUMMARY

Exemplary embodiments relate to methods and systems for analyzing tissue features based on multiplexed biometric images. Some exemplary embodiments include identifying a combination of a cell feature for biomarker expression and a normalized expression cutoff that most closely correlates a percentage of cells defined as positive for expression of the biomarker by the cell feature (a "positive cell percentage") with a field of view-level assessment across all fields of view or with a patient-level assessment across all patients.

An exemplary embodiment is a computer-implemented method that includes storing a data set in a non-transitory computer-readable medium. The data set includes cell profile data for at least one biomarker with respect to a plurality of fields of view and an association of the cell profile data with meta-information including an assessment for each field of view. The cell profile data includes biomarker expression intensity data for a plurality of cell features in a field of view. The biomarker expression intensity data is obtained from multiplexed biometric images capturing the expression of the biomarker with respect to a field of view in which individual cells are delineated and segmenting into compartments.

In some embodiments, the plurality of cell features may include a cell compartment-level expression intensity of the biomarker for a plurality of different types of cell compartments. The plurality of cell features may be selected from a group consisting of: a median biomarker expression intensity of the whole cell, a nucleus biomarker expression intensity, a membrane biomarker expression intensity, and a cytoplasm biomarker expression intensity. In some embodiments, the meta-information may include an assessment for each field of view may be a designated tissue grade for the field of view. The meta-information may include a diagnosis or a prognosis based on the field of view.

The method further includes normalizing the biomarker expression intensity data for a first cell feature in the plurality of cell features across the plurality of fields of view to obtain a distribution of normalized expression values for the first cell feature for each field of view. In some embodiments, the normalizing may include taking a logarithm of the biomarker expression intensity data for the first cell feature for each field of view to obtain a distribution of log biomarker expression intensity data for the first cell feature for each field of view. The normalizing may also include shifting the distribution of log biomarker intensity expression data for the first cell feature for each field of view such that a median of each distribution is at the same numerical value for all fields of view to produce a distribution of normalized expression values for the first cell feature for each field of view.

The method further includes calculating a plurality of threshold values for the first cell feature from a plurality of normalized expression cutoffs applied to the distributions of normalized expression values for all fields of view. The method also includes determining a plurality of positive cell percentages for the first cell feature for each field of view. Each positive cell percentage in the plurality of positive cell percentages corresponds to a threshold value in the plurality of threshold values applied to the distribution of normalized expression values for the first cell feature for the field of view. The method further includes correlating the positive percentages for each threshold value for the first feature with the meta-information for the fields of view.

The method also includes repeating the normalizing, calculating, determining, and correlating steps for a second cell feature. In some embodiments, the method includes repeating the normalizing, calculating, determining, and correlating steps for a third cell feature. After the normalizing, determining, and correlating, a combination of one of the plurality of cell features and one of the plurality of normalized expression cutoffs is identified that most closely correlates the positive cell percentages with the meta-information for the fields of view.

In some embodiments, the method may further include creating cell profile data. Creating cell profile data may include obtaining images of a tissue sample of a patient from which multiplexed biometric images are produced. Creating cell profile data may further include delineating individual cells and segmenting the cells into compartments in a field of view of an image of a tissue sample for a plurality of images of tissue samples to produce multiplexed biometric images from which biomarker expression intensity data is obtained.

Another example embodiment includes a computer-implemented method of analyzing tissue features with respect to a plurality of biomarkers based on multiplexed biometric images. The method includes storing a data set in a non-transitory computer-readable medium. The data set includes cell profile data for a plurality of biomarkers with respect to a plurality of fields of view and an association of the cell profile data with meta-information including an assessment for each field of view. The cell profile data includes biomarker expression intensity data for at least one cell feature in a field of view. The biomarker expression intensity data is obtained from multiplexed biometric images capturing the expression of the plurality of biomarkers with respect to a field of view in which individual cells are delineated and segmenting into compartments.

The method further includes, normalizing the biomarker expression intensity data for a first cell feature and a first biomarker across the plurality of fields of view to obtain a distribution of normalized expression values for the first cell feature for each field of view. The method also includes, for each biomarker, calculating a plurality of threshold values for the first cell feature and the first biomarker from a plurality of normalized expression cutoffs applied to the distributions of normalized expression values for all fields of view. The method also includes determining a plurality of positive cell percentages for the first cell feature for each field of view. Each positive cell percentage in the plurality of positive cell percentages corresponds to a threshold value applied to the distribution of normalized expression values for the first cell feature for the field of view. The method further includes, correlating the positive percentages for each threshold value for the first feature and the first biomarker with the meta-information for the fields of view. The method includes repeating the normalizing, calculating, determining and correlating steps for a second biomarker. In some embodiments, the method may also include repeating the normalizing, calculating, determining, and correlating steps for a second cell feature. The method may further include repeating the normalizing, calculating, determining, and correlating steps for a third cell feature. After the normalizing, calculating, determining, and correlating steps, a combination of a cell feature of one of the plurality of biomarkers and one of the plurality of normalized expression cutoffs is identified that most closely correlates the positive cell percentages with the meta-information for the fields of view.

Another exemplary embodiment includes a computer-implemented method of analyzing tissue features based on multiplexed biometric images. The method includes storing a data set including cell profile data for at least one biomarker with respect to a plurality of fields of view in a non-transitory computer-readable medium. The cell profile data includes biomarker expression intensity data for a plurality of cell features in a field of view. The biomarker expression intensity data is obtained from multiplexed biometric images from a plurality of patients. The multiplexed biometric images capture the expression of the biomarker with respect to a field of view in which individual cells are delineated and segmenting into compartments. The data set further includes an association of the cell profile data with meta-information including an assessment for each patient. In some embodiments, the meta-information may include a diagnosis or a prognosis for each patient. In some embodiments, the meta-information may include a survival time for the patient.

The method also includes normalizing the biomarker expression intensity data for a first cell feature in the plurality of cell features across the plurality of fields of view to obtain a distribution of normalized expression values for the first cell feature for each field of view. The method further includes calculating a plurality of threshold values for the first cell feature from a plurality of normalized expression cutoffs applied to the distributions of normalized expression values for all fields of view.

The method further includes, determining a plurality of positive cell percentages for the first cell feature for each patient. Each positive cell percentage in the plurality of cell percentages corresponds to a threshold value applied to distributions of normalized expression values for the first cell feature for all of fields of view associated with the patient. The method also includes correlating the positive percentages for each threshold value for the first feature with the meta-information across for the patients. The method further includes repeating the normalizing, calculating, determining, and correlating steps for a second cell feature. In some embodiments, the method includes repeating the normalizing, calculating, determining, and correlating steps for a third cell feature. A combination of one of the plurality of cell features and one of the plurality of normalized expression cutoffs that most closely correlates the positive cell percentages with the meta-information for the patients is identified.

Another exemplary embodiment includes a computer-implemented method of analyzing tissue features based on multiplexed biometric images. The method includes storing a data set including cell profile data for a plurality of biomarkers with respect to a plurality of fields of view in a non-transitory computer-readable medium. The cell profile data includes biomarker expression intensity data for at least one cell feature in a field of view. The biomarker expression intensity data is obtained from multiplexed biometric images from a plurality of patients. The multiplexed biometric images capture the expression of the biomarker with respect to a field of view in which individual cells are delineated and segmenting into compartments. The data set further includes an association of the cell profile data with meta-information including an assessment for each patient. In some embodiments, the meta-information may include a diagnosis or a prognosis for each patient. In some embodiments, the meta-information may include a survival time for the patient.

The method also includes, normalizing the biomarker expression intensity data for a first cell feature and a first biomarker across the plurality of fields of view to obtain a distribution of normalized expression values for the first cell feature and the first biomarker for each field of view. The method further includes, calculating a plurality of threshold values for the first cell feature and the first biomarker from a plurality of normalized expression cutoffs applied to the distributions of normalized expression values for all fields of view.

The method further includes, determining a plurality of positive cell percentages for the first cell feature and the first biomarker for each patient. Each positive cell percentage in the plurality of cell percentages corresponds to a threshold value applied to distributions of normalized expression values for the first cell feature and the first biomarker for all of fields of view associated with the patient. The method also includes correlating the positive percentages for each threshold value for the first feature and the first biomarker with the meta-information for all the patients. The method further includes repeating the normalizing, calculating, determining, and correlating steps for a second biomarker. In some embodiments, the method further includes repeating the normalizing, calculating, determining, and correlating steps for a second cell feature. In some embodiments, the method includes repeating the normalizing, calculating, determining, and correlating steps for a third cell feature. The method further includes identifying a combination of a cell feature for one of the plurality of biomarkers and one of the plurality of normalized expression cutoffs that most closely correlates the positive cell percentages with the meta-information for the patients.

Other embodiments include systems for performing the methods. A system for analyzing tissue features based on multiplexed biometric image data may include a storage device for storing the data set and at least one processor for executing code that causes the at least one processor to perform the steps of the method.

BRIEF DESCRIPTION OF DRAWINGS

Features and aspects of embodiments are described below with reference to the accompanying drawings.

FIG. 11 is a plot of the fraction of positive cells per FOV, grouped by normal FOVs and cancerous FOVs, for the biomarker NaKATPase expressed in the cytoplasm with the normalized expression cutoff set at 85% of the cells being negative across all FOVs.

FIG. 12 is a plot of the logarithm of odds of a FOV being normal as a function of the fraction of positive cells in the FOV for the biomarker NaKATPase expressed in the cytoplasm at an 85% negative cutoff.

FIG. 13 is a plot of the fraction of positive cells per FOV, grouped by normal FOVs and cancerous FOVs, for the biomarker EGFR expressed in the membrane at a 95% negative cutoff.

FIG. 14 is a plot of the logarithm of odds of a FOV being normal as a function of the fraction of positive cells in the FOV for biomarker EGFR expressed in the membrane at a 95% negative cutoff.

FIG. 15 is a plot of the fraction of positive cells per FOV, grouped by normal FOVs and cancerous FOVs, for the biomarker S6 expressed in the cytoplasm at an 80% negative cutoff.

FIG. 16 is a plot of the logarithm of odds of a FOV being normal as a function of the fraction of positive cells in the FOV for the biomarker EGFR expressed in the cytoplasm at a 95% negative cutoff.

FIG. 20 is a plot of the fraction of positive cells for each patient, grouped by patients that survived five years (alive), and for patients that did not (dead), for expression of biomarker S6 in the cytoplasm with the normalized expression cutoff set at 90% of cells being negative across all FOVs.

FIG. 21 is a plot of the logarithm of odds of a patient surviving five years as a function of the fraction of positive cells for expression of S6 in the cytoplasm at a 90% negative cutoff.

FIG. 22 is a plot of the fraction of positive cells for each patient for expression of biomarker NaKATPase at a 90% cutoff.

FIG. 23 is a plot of the logarithm of odds of a patient surviving five years as a function of the fraction of positive cells for expression of NaKATPase in the cytoplasm at a 90% negative cutoff.

FIG. 24 is a plot of the fraction of positive cells for each patient for expression of Keratin at a 99% negative cutoff.

FIG. 25 is a plot of the logarithm of odds of a patient surviving 5 years as a function of the fraction of positive cells for each patient for expression of Keratin in the cytoplasm at a 99% negative cutoff.

DETAILED DESCRIPTION

Some embodiments described herein relate to methods of analyzing tissue features based on multiplexed biometric images by identifying a combination of a cell feature among a plurality of cell features (e.g., expression of a biomarker in a cellular compartment) and a normalized expression cutoff among a plurality of normalized expression cutoffs (e.g., a percentage of positive cells across all fields of view) that most closely correlates a percentage of positive cells for a field of view (FOV) with meta-information, such as a determined assessment for the FOV (e.g., a Gleason score). Some embodiments described herein relate to methods of analyzing tissue features by identifying a combination of a cell feature and a normalized expression cutoff that most closely correlates percentages of positive cells in FOVs associated for a patient with meta-information for the patient (e.g., a survival time). Identified combinations of a cell feature and a normalized expression cutoff for one or more biomarkers, determined using embodiments, may be employed in models for assessment and/or diagnosis of tissue samples at a FOV level and/or at a patient level.

Figure 1:
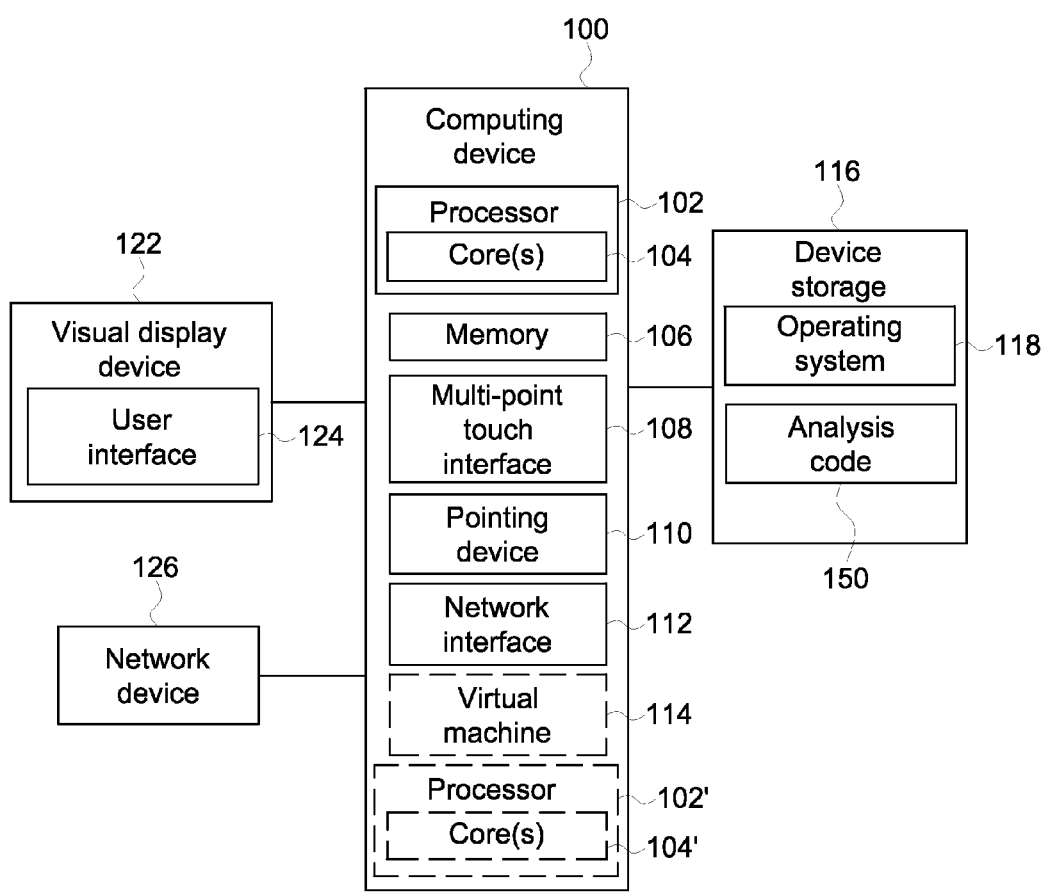
FIG. 1 illustrates an exemplary computing environment suitable for practicing exemplary embodiments taught herein.

FIG. 1 illustrates an exemplary computing environment suitable for practicing exemplary embodiments taught herein. The environment includes a computing device 100 with associated peripheral devices. Computing device 100 is programmable to implement executable code 150 for various methods as taught herein. Computing device 100 includes a storage device 116, such as a hard-drive, CD-ROM, or other non-transitory computer readable media. Storage device 116 stores an operating system 118 and other related software. Computing device 100 may further include memory 106. Memory 106 may comprise a computer system memory or random access memory, such as DRAM, SRAM, EDO RAM, etc. Memory 106 may comprise other types of memory as well, or combinations thereof. Computing device 100 may store, in storage device 116 and/or memory 106, instructions for implementing and processing every module of the executable code 150.

Computing device 100 also includes processor 102, and may include one or more additional processor(s) 102', for executing software stored in the memory 106 and other programs for controlling system hardware. Processor 102 and processor(s) 102' each can be a single core processor or multiple core (104 and 104') processor. Virtualization may be employed in computing device 100 so that infrastructure and resources in the computing device can be shared dynamically. Virtualized processors may also be used with executable analysis code 150 and other software in storage device 116. A virtual machine 114 may be provided to handle a process running on multiple processors so that the process appears to be using only one computing resource rather than multiple. Multiple virtual machines can also be used with one processor.

A user may interact with computing device 100 through a visual display device 122, such as a computer monitor, which may display the user interfaces 124 or any other interface. The visual display device 122 may also display other aspects or elements of exemplary embodiments, e.g. an icon for storage device 116. Computing device 100 may include other I/O devices such a keyboard or a multi-point touch interface 108 and a pointing device 110, for example a mouse, for receiving input from a user. The keyboard 108 and the pointing device 110 may be connected to the visual display device 122. Computing device 100 may include other suitable conventional I/O peripherals.

Computing device 100 may include a network interface 112 to interface with a network device 126 via a Local Area Network (LAN), Wide Area Network (WAN) or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, controller area network (CAN), or some combination of any or all of the above. The network interface 112 may comprise a built-in network adapter, network interface card, PCMCIA network card, card bus network adapter, wireless network adapter, USB network adapter, modem or any other device suitable for enabling computing device 100 to interface with any type of network capable of communication and performing the operations described herein.

Moreover, computing device 100 may be any computer system such as a workstation, desktop computer, server, laptop, handheld computer or other form of computing or telecommunications device that is capable of communication and that has sufficient processor power and memory capacity to perform the operations described herein.

Computing device 100 can be running any operating system 118 such as any of the versions of the MICROSOFT WINDOWS operating systems, the different releases of the Unix and Linux operating systems, any version of the MACOS for Macintosh computers, any embedded operating system, any real-time operating system, any open source operating system, any proprietary operating system, any operating systems for mobile computing devices, or any other operating system capable of running on the computing device and performing the operations described herein. The operating system may be running in native mode or emulated mode.

Embodiments taught herein leverage multiplexed biometric images that are generated through known techniques, such as such as through a multiplexing staining-destaining technique. The images illustrate the expression of one or more biomarkers within individual cells that enables comparison of the individual cells to each other. The individual cells are part of a larger cell sample. For example, the cell sample may be a group of cells from a cell culture, a tissue sample, organ, tumor, or lesion. Some or all of the individual cells may be part of a group of specimens of similar tissue from different subjects. These groups of specimens may represent one or more disease or condition models, different stages within a disease or condition model, and/or one or more responses to treatment of a disease or condition.

Images of each stained FOV are generated through known techniques, such as with a digital camera coupled with an appropriate microscope and appropriate quality control routines. Automated image registration and analysis may also be used to quantify the biomarker concentration levels for individual delineated cells, or even sub-cellular compartments, such as nucleus, cytoplasm, and membrane. The data values resulting from the multiplexing and image analysis of cells may be stored alone or in conjunction with data that is the result of further analysis. The database may preserve the identity of the measurement of strength of the biomarker expression including the tissue and the location within the tissue from which it was drawn. The location includes the particular cell from which a particular measurement was drawn and may also include the compartment, nucleus, cytoplasm or membrane, associated with the measurement. The information is stored in a database which may be maintained in a storage device 116 or in a network device 126.

Figure 2:
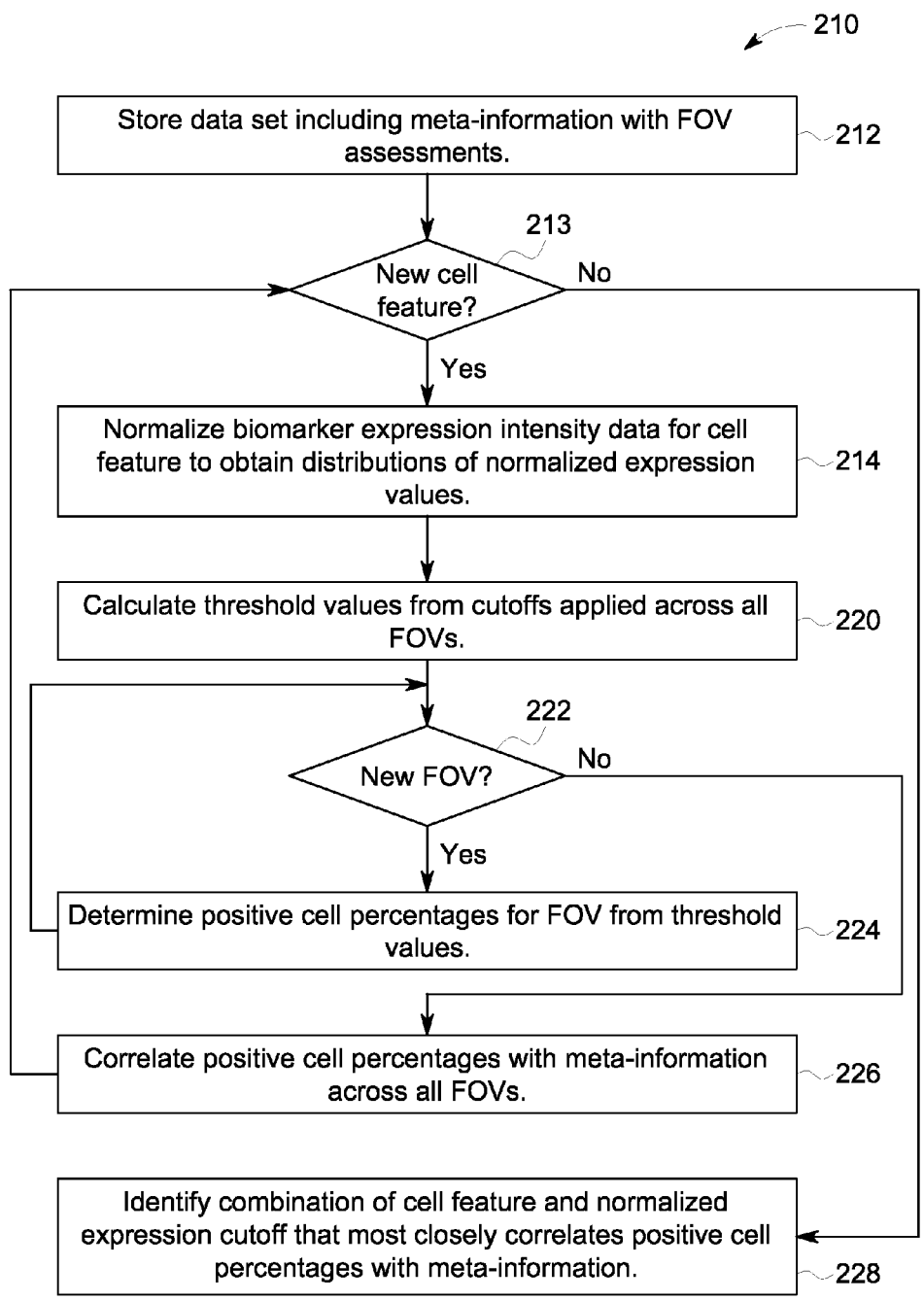
FIG. 2 illustrates an exemplary method of analyzing tissue features by identifying a combination of cell feature and a normalized expression cutoff for expression of a biomarker that correlates positive cell percentages with field-of view level assessments across a plurality of fields of view (FOVs).

FIG. 2 illustrates a method 210 for identifying a normalized expression cutoff for biomarker expression in cells and/or cell compartments that, when applied to a FOV, results in a positive cell percentage for the FOV that correlates with an assessment of the FOV. As used herein, the term "cutoff" alone refers to a normalized expression cutoff. In step 212, a data set including cell profile data for at least one biomarker with respect to a plurality of fields of view (FOVs) is stored in a computer readable medium (e.g., storage device 116 or network device 126). The cell profile data includes biomarker expression intensity data for a plurality of cell features in a FOV. Examples of cell features that may be included in the plurality of cell features include average or median biomarker expression intensity data for each cell, and average or median biomarker intensity data for one or more types of cell compartments within each cell (e.g., cytoplasm, nucleus, and membrane). In some embodiments, the plurality of cell features may include a cell compartment-level expression intensity of a biomarker for a plurality of different types of cell compartments. The plurality of cell features may be selected from a group including: a median biomarker expression intensity of the whole cell, a nucleus biomarker expression intensity, a membrane biomarker expression intensity, and a cytoplasm biomarker expression intensity.

In some embodiments, the cell features may include a ratio of expression intensity in one cell compartment relative to expression intensity in one or more other cell compartments, relative to overall expression in the cell, or relative to average expression for all cells in a FOV. For example, in some embodiments, the plurality of cell features may include a nucleus intensity ratio, a membrane intensity ratio, and a cytoplasm intensity ratio, where the three compartment ratios relate the median intensity of the expression of the nucleus, membrane, or cytoplasm to the average median intensity of the other two compartments.

The biomarker expression intensity data may be obtained from multiplexed biometric images capturing the expression of at least one biomarker with respect to a FOV in which individual cells are delineated and segmented into compartments. The data set also includes an association of the cell profile with meta-information including an assessment for each FOV. The assessment may be for example, a designated tissue grade (e.g., Gleason score) of the FOV. The assessment for each FOV may include a diagnosis or a prognosis.

The cell profile data is generated from a plurality of tissue samples drawn from a plurality of patients. At least some of the plurality of patients may have a commonality, for example, at least some of the patients may share a disease or condition. Alternatively, the commonality may be, for example, that the patients share a preliminary diagnosis of the same disease or condition. The assessment may be related to the commonality (e.g., a Gleason score).

In some embodiments, method 210 may include obtaining images of a tissue sample of a patient from which multiplexed biometric images are produced. Method 210 may include delineating individual cells and segmenting the cells into compartments in a FOV of an image of a tissue sample for a plurality of images of tissue samples to produce the multiplexed biometric images. Method 210 may include creating the cell profile data from the multiplexed biometric images.

U.S. Patent Application Publication No. US2011/0091081, entitled "Method and System for Analyzing the Expression of Biomarkers in Cells in Situ in Their Tissue of Origin," and U.S. Patent Application Publication No. US2011/0091091, entitled "Process and System for Analyzing the Expression of Biomarkers in Cells," each of which is incorporated herein in its entirety, describe methods of generating biomarker expression intensity data for various different cell features (e.g., cell compartment expression, overall cell expression) for a plurality of biomarkers from multiplexed biometric images.

U.S. Patent Publication No. US2011/0091081 discloses a process for acquiring data for analysis of the patterns of expression of multiple biomarkers in cells in their tissue of origin. The level of expression of multiple biomarkers in individual cells or in the subcellular compartments of the individual cells in situ in the tissue of origin was measured. The measurements were made by treating the tissue specimens with antibodies or antibody surrogates specific to the biomarkers of interest. The antibodies or antibody surrogates were directly or indirectly labeled with moieties that give off optical signals when interrogated with light of the appropriate wavelength. The tissue specimens were repeatedly treated, with each treatment involving antibodies or antibody surrogates specific to different biomarkers than those involved in any other treatment and the signal generation from the immediately previous treatment was neutralized by optical or chemical means. The amount of each label bound to the biomarkers of interest by the antibodies or antibody surrogates was measured by subjecting the specimen to light of the appropriate wavelength and digitally imaging the response. The cells were segmented into individual cell units and their subcellular compartments (including membrane, cytoplasm and nucleus) were part of the data acquisition. The database stored the original measurement values and the location, cell or compartment of the cell, from which each measurement is drawn.

Figure 3:
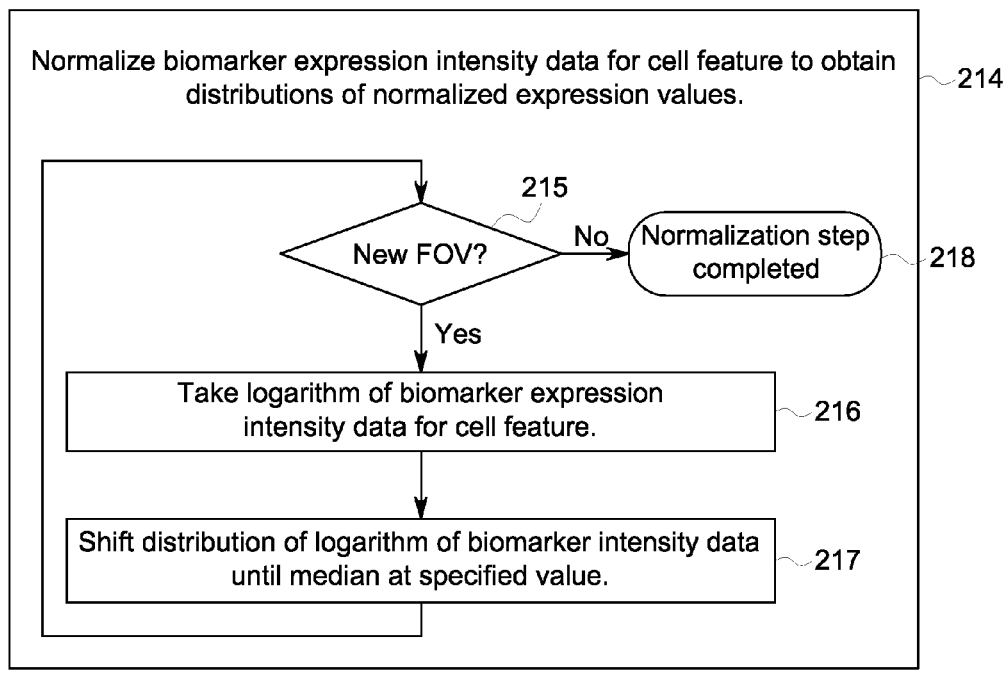
FIG. 3 further illustrates steps that may be incorporated in the normalization step of the method of FIG. 2.

As indicated by decision block 213, for each cell feature in the plurality of cell features, a number of steps including steps 214, 220, 224, and 226 are performed. In step 214, the biomarker expression intensity data for the cell feature is normalized across the plurality of FOVs to obtain a distribution of normalized expression values for the cell feature for each FOV. An example of steps that may be included in the normalization step, in accordance with some embodiments, is shown in FIG. 3. In step 216 of FIG. 3, a logarithm is taken of the biomarker expression intensity data for the cell feature to obtain a distribution of log biomarker expression intensity data for the FOV. In step 217, the distribution of log biomarker expression intensity data for the cell feature is shifted (e.g., by addition or subtraction of a constant) such that a median of the distribution for the FOV is at a specified value. When the expression values are depicted on a log scale of the expression intensity of a biomarker in the image, a subtraction or addition of a constant on the log scale corresponds to a division or multiplication by the constant in the original expression intensity measurement scale. As indicated by decision block 215, steps 216 and 217 are repeated for each FOV. In step 217, the distribution of log biomarker expression intensity data for the cell feature for the FOV is shifted such that the median of the distribution is at the same specified value for all FOVs. The normalization step ends at 218 when steps 216 and 217 have been performed for all FOVs for a cell feature. In other embodiments, the steps may occur in a different order. For example, step 216 may be performed for all FOVs before step 217 is performed for all the FOVs. An example of normalization with respect to expression of the biomarker NaKATPase in the cytoplasm of cells is described below with respect to FIGS. 7-9.

In other embodiments, the biomarker expression intensity data for a cell feature may be normalized using other methods. Some embodiments may normalize the expression intensity values to determine the median intensity of a whole cell's expression for all cells within a batch of measurements and subtract this median value from each measurement value in the batch. Such median intensity may apply to the expression of a specific biomarker. This normalized or standardized value may be stored in the database or generated as part of the processing of the data set in the database. Other embodiments may involve more normalization, less normalization or different normalization of the data collected.

In some embodiments, the distributions of normalized expression values may be generated from a filtered data set.

Such filtering may be done as a quality control measure. For example, the filtering may exclude cell profile data related to cells including at least one compartment represented by fewer than a threshold number of pixels in the multiplexed image.

Turning again to method 210 depicted in FIG. 2, in step 220, a plurality of threshold values are calculated from a plurality of normalized expression cutoffs applied to the distributions of normalized expression values for the FOVs. Normalized expression cutoffs may also be referred to simply as "cutoffs." Each normalized expression cutoff for a biomarker and a cell feature may be described in terms of a total proportion of cells across all FOVs that are defined to be positive, or in terms of a total proportion of cells across all FOVs that are defined to be to be negative. For example, a set of normalized expression cutoffs for expression of biomarker NaKATPase in the cytoplasm may define 20%, 15%, 10%, 5%, and 1% of cells across all fields of view to be positive. This may be described as cutoffs at 20% positive, at 15% positive, at 10% positive, at 5% positive, and at 1% positive. The same concept can be expressed as a set of negative cutoffs defining 80%, 85%, 90%, 95%, and 99% of cells across all fields of view to be negative. This may be described as cutoffs at 80%, at 85% negative, at 90% negative, at 95% negative, and at 99% negative. More or fewer cutoffs than 5 may be considered. For example, 3, 4, 7, 10, 15, or 20 cutoffs may be considered. At some level, however, applying many different cutoffs may not be particularly valuable. For example, very similar results may be obtained by applying an 85% cutoff and an 86% cutoff. Similarly, different ranges of cutoffs may be considered. For example, all cutoffs may fall within a range of 95% and 99%.

Application of a normalized expression cutoff (e.g., 20% positive) across distributions of normalized expression values for all FOVs yields a number for the threshold value (e.g., 1.2). An example of a normalized expression cutoff applied to distributions of normalized expression values to calculate a threshold value is described below with respect to FIG. 9.

After a plurality of threshold values are calculated from a plurality of normalized expression cutoffs applied to distributions of normalized expression values across all FOVs in step 220, the plurality of threshold values are applied to the distribution of normalized expression values for a FOV in step 224, thereby determining a plurality of positive cell percentages for the FOV. Applying a threshold value to a FOV yields a percentage of positive cells for the FOV, which reflects the proportion of cells in the individual FOV that exceed the threshold value for expression of the biomarker by the specified cell feature. A plurality of threshold values applied to a FOV produces a plurality of positive percentages for the FOV. As indicated by the loop including decision block 222, determining step 224 is repeated for all FOVs.

After positive cell percentages have been determined for all FOVs, the positive cell percentages for each threshold value are correlated with meta-information (including assessments) for the FOVs across all FOVs in step 226. A correlation between positive cell percentages for FOVs for a particular normalized expression cutoff-threshold value and assessments for FOVs can be derived by fitting a classification model with the assessments as the outcome and positive cell percentages as the predictors. Several classification analysis frameworks exist, including, but not limited to: random forests, neural networks, logistic regression models, multinomial logistic regression models, random survival forests, empirical Kaplan-Meier curves, log rank tests, and Cox proportional hazards models. For example, correlations between tissue grade and a positive cell percentages for a feature are derived, in some embodiments, by fitting a random forest classification model, neural network model or multinomial logistic regression model with tissue grades as the outcome and positive cell percentages as predictors. Logistical regression may be used to predict two classes, such as whether or not a patient survived 5 years. As another example, a random survival forest model, empirical Kaplan-Meier curves, log rank tests or a Cox proportional hazards model may be used to correlate a positive cell percentages for FOVs and assessments with ranges of survival time. In some embodiments, the positive cell percentages are examined for a univariate correlation with an assessment. In other embodiments, the positive cell percentages are examined for a multivariate correlation with an assessment.

As indicated by decision block 213, the normalizing step 214, calculating step 220, determining step 224, and correlating step 226 may be performed for one or more additional cell features (e.g., a second cell feature, a third cell feature, a median expression of the biomarker for the whole cell). For example, the first cell feature may be expression of a biomarker in the nucleus of a cell, the second cell feature may be expression of the biomarker in the cytoplasm of the cell, and the third cell feature may be expression of the biomarker in the membrane of the cell.

In step 228, a combination of one of the plurality of cell features and one of the plurality of normalized expression cutoff that most closely correlates the positive cell percentages for the with the meta-information for the FOVs is identified. Method 210 identifies a combination of expression of a biomarker by a cell feature (e.g., cytoplasm expression) and a normalized expression cutoff (e.g., 80% negative) that can be used to define which cells are positive for the biomarker in each FOV. An exemplary identified combination, namely expression of NaKATPase in the cytoplasm with the cutoff at 85% negative (15% positive) is described below with respect to FIGS. 10, 11 and 12. The identified combination may be referred to as a "predictive" combination because the combination produces cell percentages that accurately predict outcomes when used as predictors in a classification model. The identified normalized expression cutoff can be applied to data for cell feature expression of the biomarker for additional FOVs and the resulting positive cell percentages used to predict assessments of the additional FOVs (e.g., a Gleason score of the FOV).

Although method 210 is described above with respect to one biomarker, in some embodiments, a method of analyzing tissue features may incorporate analysis with respect to a plurality of biomarkers. An example embodiment of a method 230 for analyzing tissue features by identifying a combination of a cell feature of one of a plurality of biomarkers and a normalized expression cutoff that correlates positive cell percentages with assessments across a plurality of FOVs is depicted in FIG. 4.

Figure 4:
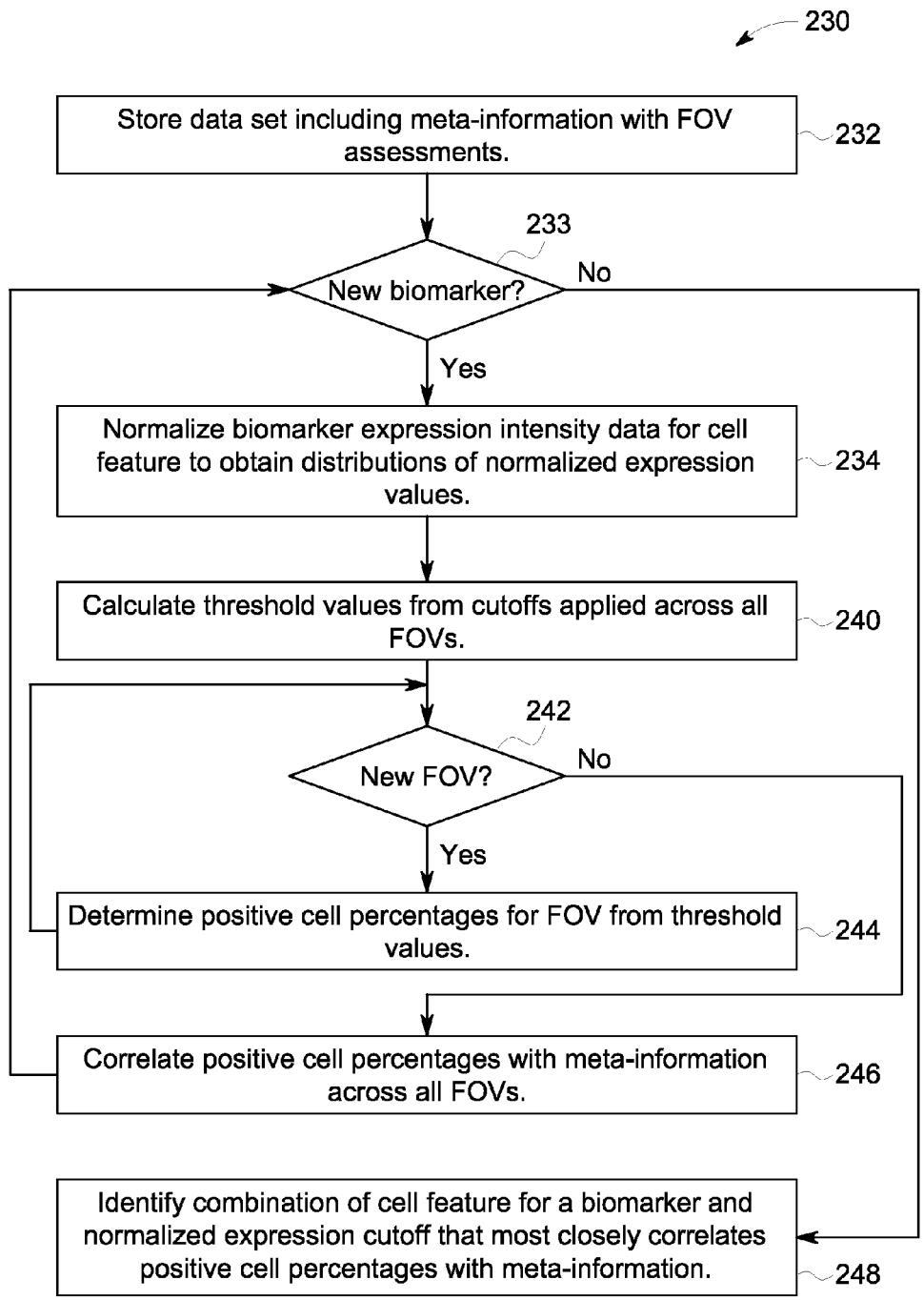
FIG. 4 illustrates an exemplary method of analyzing tissue features by identifying a combination of a cell feature of one of a plurality of biomarkers and a normalized expression cutoff for that correlates positive cell percentages with field-of view level assessments across a plurality of FOVs.

In step 232 of FIG. 4, a data set including cell profile data for a plurality of biomarkers with respect to a plurality of FOVs is stored in a computer readable medium (e.g., storage device 116 or network device 126). The cell profile data includes biomarker expression intensity data for at least one cell feature (e.g., expression in the cytoplasm, expression in the membrane, expression in the nucleus). The biomarker expression intensity data may be obtained from multiplexed biometric images capturing the expression of the plurality of biomarkers with respect to a FOV in which individual cells are delineated and segmented into compartments. The data set also includes an association of the cell profile data with meta-information including an assessment for each FOV.

For each biomarker, a set of steps including a normalization step 234, a calculation step 240, a determination step 244, and a correlation 246 step are performed, as indicated by decision block 233. In step 234, the biomarker expression intensity data for a cell feature is normalized across the plurality of FOVs to obtain a distribution of normalized expression values for the cell feature for each FOV. Normalization step 234 may take a variety of different forms, such as steps 216 and 217 of FIG. 3.

In step 240, a plurality of threshold values is calculated from a plurality of normalized expression cutoffs applied across all FOVs. In step 244, the plurality of threshold values are applied to the distribution of normalized expression values for a FOV to determine a plurality of positive cell percentages for the cell feature for the FOV. As indicated by decision block 242, step 244 is performed for all FOVs resulting in a plurality of positive cell percentages for each FOV. In step 246, the positive cell percentages for each threshold value are correlated with the meta-information across all FOVs. In some embodiments, steps 234, 240, 244, and 246 may be performed for one or more additional cell features for each biomarker.

In step 258, a combination of a cell feature for expression of one of the plurality of biomarkers and one normalized expression cutoff is identified that most closely correlates the positive cell percentages with the meta-information across the FOVs. Various exemplary identified combinations of normalized expression cutoffs and cell features different biomarkers are described below with respect to FIG. 10.

Figure 5:
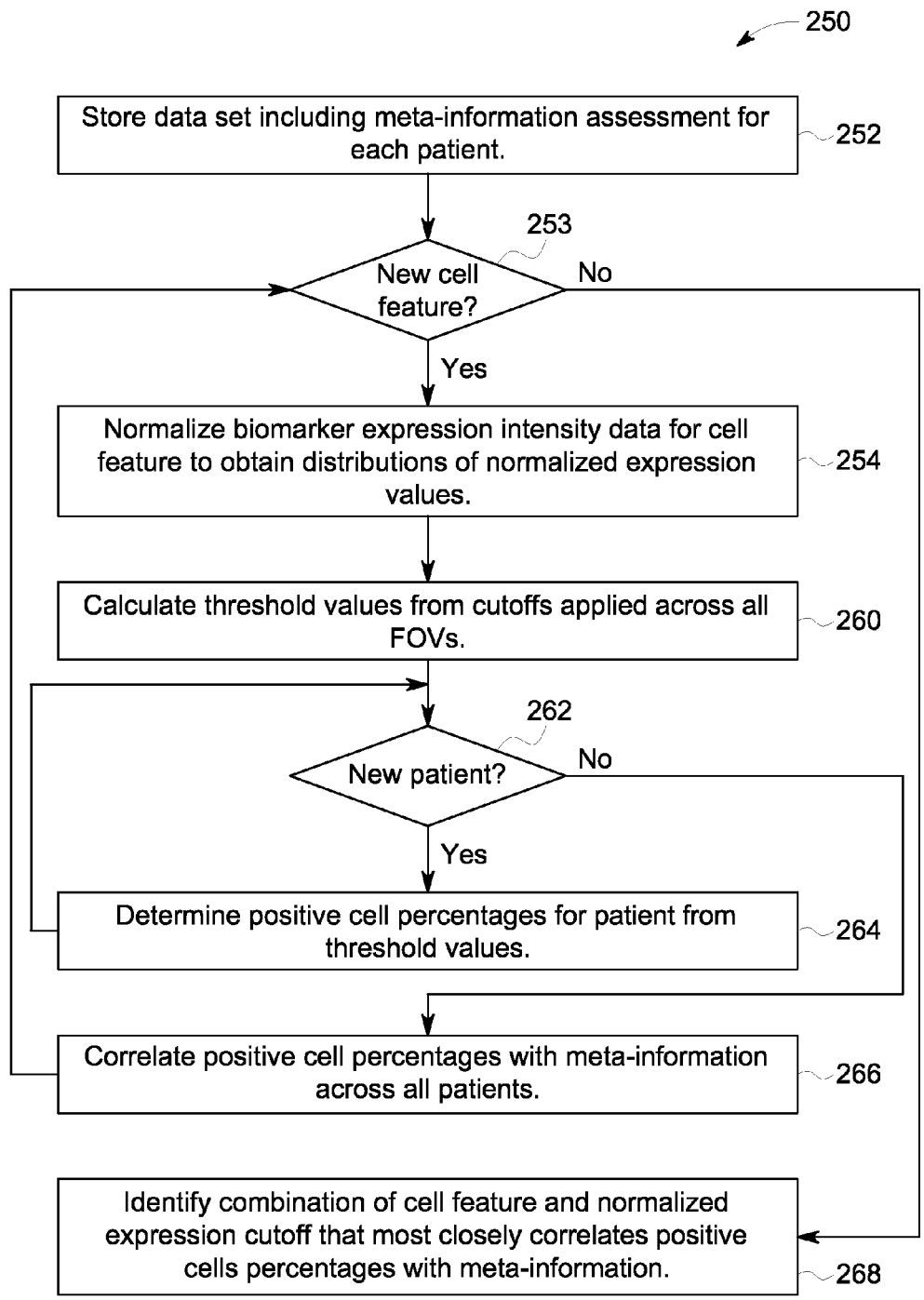
FIG. 5 illustrates an exemplary method of analyzing tissue features by identifying a combination of a cell feature and a normalized expression cutoff for expression of a biomarker that correlates positive cell percentages with patient-level assessments across a plurality of patients.

Although methods 210 and 230 involve determining and correlating steps performed at a FOV-level, in some embodiments, a determining step and a correlating step may be performed at a patient-level, such as method 250 in FIG. 5. In step 252 of FIG. 5, a data set including cell profile data for at least one biomarker with respect to a plurality of fields of view is stored. The biomarker expression intensity data is obtained from multiplexed biometric images from a plurality of patients. The multiplexed biometric images capture the expression of the biomarker with respect to a FOV in which individual cells are delineated and segmenting into compartments. The data set also includes an association of the cell profile data with meta-information including an assessment for each patient. The assessment may be a diagnosis or a prognosis, (e.g., a survival time after diagnosis).

In step 254, the biomarker expression intensity data for a cell feature across the plurality of fields of view is normalized to obtain a distribution of normalized expression values for the cell feature for each FOV. The normalization step 254 may take a variety of different forms, such as steps 216 and 217 of FIG. 3.

In step 260, a plurality of threshold values for the cell feature are calculated from a plurality of normalized expression cutoffs applied across all fields of view. As noted above, the normalized expression cutoffs may be described in terms of a normalized expression cutoff for a total proportion of cells across all FOVs defined to be positive for cell feature, or in terms of a normalized expression cutoff for a total proportion of cells across all FOVs that are defined to be negative for the cell feature.

After threshold values of the normalized expression cutoffs are calculated, each threshold value is applied to the distributions of normalized expression values for all FOVs associated with a patient. In step 264, a plurality of positive cell percentages for the cell feature is determined for a patient. Each positive cell percentage corresponds to a threshold value applied to distributions of normalized expression values for the cell feature for all FOVs associated with the patient. The application of the threshold value to all FOVs for the patient produces a positive percentage, which reflects the proportion of the cells across all of the FOVs for the patient that exceed the threshold value for expression of the biomarker in the cell feature. A plurality of threshold values applied to FOVs for a patient produces a plurality of positive percentages for the patient. As indicated by decision block 262, step 264 is performed for all patients.

In step 266, the positive cell percentages for each threshold value are correlated with the meta-information (including an assessment of the patient) across the patients. As described above, many different classification techniques may be employed to correlate the positive cell percentages with assessments.

As indicated by decision block 253, steps 254, 260, 264, and 266 are performed for each cell feature in the plurality of cell features. In step 268, a combination of a cell feature in the plurality of cell features and one normalized expression cutoff that most closely correlates the positive cell percentages with the meta-information for all patients is identified. Various exemplary identified combinations of normalized expression cutoffs and cell features for different biomarkers that were determined at a patient-level are described below with respect to FIG. 19.

Figure 6:
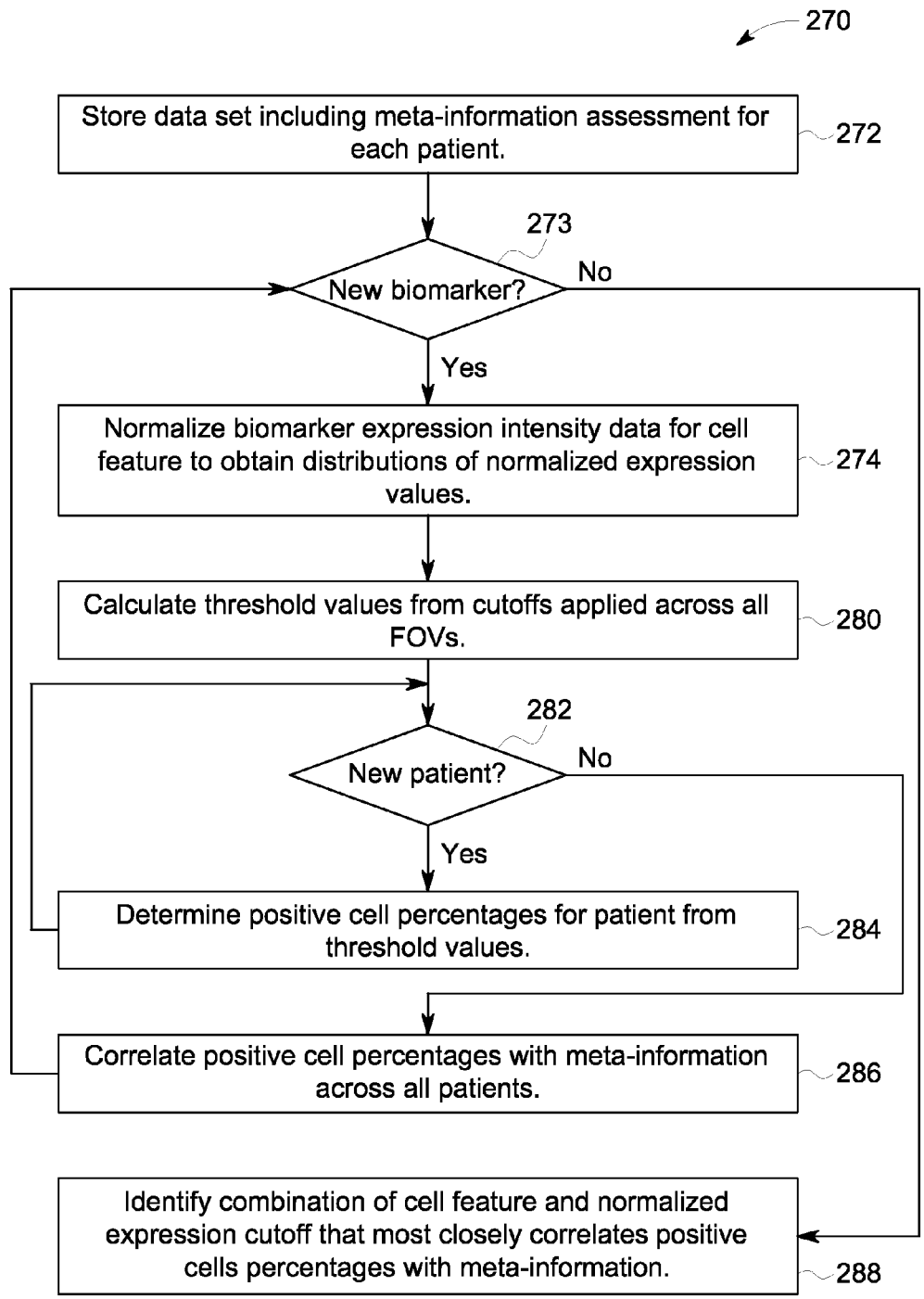
FIG. 6 illustrates an exemplary method of analyzing tissue features by identifying a combination of a cell feature of one of a plurality of biomarkers and a normalized expression cutoff for expression of a biomarker that correlates positive cell percentages with patient-level assessments across a plurality of patients.

An example embodiment of a method 270 for analyzing tissue features by identifying a combination of a cell feature of one of a plurality of biomarkers and a normalized expression cutoff that correlates positive cell percentages with assessments across a plurality of patients is depicted in FIG. 6.

In step 272, a data set is stored in a non-transitory computer-readable medium that includes cell profile data for a plurality of biomarkers with respect to a plurality of FOVs. The cell profile data includes biomarker expression intensity data for at least one cell feature in a FOV. The biomarker expression intensity data is obtained from multiplexed biometric images from a plurality of patients. The multiplexed biometric images capture the expression of the plurality of biomarkers with respect to a FOV in which individual cells are delineated and segmenting into compartments. The data set further includes an association of the cell profile data with meta-information including an assessment for each patient.

In step 274, the biomarker expression intensity data for a cell feature across the plurality of FOVs is normalized to obtain a distribution of normalized expression values for the cell feature for each FOV. The normalization step 274 may take a variety of different forms, such as steps 216 and 217 of FIG. 3.

In step 280, a plurality of threshold values for the cell feature are calculated from a plurality of normalized expression cutoffs applied across all fields of view. As noted above, the normalized expression cutoffs may be described in terms of a normalized expression cutoff for a total proportion of cells across all FOVs defined to be positive for cell feature, or in terms of a normalized expression cutoff for a total proportion of cells across all FOVs that are defined to be negative for the cell feature.

After threshold values for normalized expression cutoffs are calculated based on all fields of view, each threshold value is applied to the distributions of normalized expression values for all FOVs associated with a patient. In step 284, a plurality of positive cell percentages for the cell feature determined for a patient. Each positive cell percentage corresponds to a threshold value applied to distributions of normalized expression values for the cell feature for all FOVs associated with the patient. The application of the threshold value to all FOVs for the patient produces a positive percentage, which reflects the proportion of the cells across all of the FOVs for the patient that exceed the threshold value for expression of the biomarker in the cell feature. A plurality of threshold values applied to FOVs for a patient produces a plurality of positive percentages for the patient. As indicated by decision block 282, step 284 is performed for all patients.

In step 286, the positive cell percentages for each threshold value are correlated with the meta-information (including an assessment of the patient) across the patients. As described above, many different classification techniques may be employed to correlate the positive cell percentages with assessments.

As indicated by decision block 273, steps 274, 280, 284, and 286 are performed for each biomarker in the plurality of biomarkers. In step 288, a combination of a cell feature for one of the biomarkers and one normalized expression cutoff that most closely correlates the positive cell percentages with the meta-information for all patients is identified. In some embodiments, steps 273, 280, 284 and 286 may be performed for a plurality of cell features for each biomarker. Various exemplary identified combinations of normalized expression cutoffs, cell features and biomarkers determined at a patient-level are described below with respect to FIG. 19.

Although FIGS. 2-6 are illustrated with steps connected by arrows, exemplary embodiments should not be limited to the specific order of or arrangement of steps depicted. For example, the normalization step 214 of method 210 may be performed for multiple different cell features before the calculating step 220 is performed for any of the cell features. The normalizing step 214, the calculating step 220, determining step 224 and the correlating step 226 may be performed for different cell features at the same time (e.g., in parallel). As another example, in method 230, the normalizing 234, normalizing step 234, the calculating step 240, the determining step 244, and the correlating step 246 may be performed sequentially for different biomarkers, in parallel for different biomarkers, or any combination of the aforementioned. Further, each "step" may incorporate sub-steps. The "steps" may be grouped together in various different combinations.

Additional embodiments include systems for analyzing tissue features based on multiplexed biometric image data. For example, additional embodiments may implement any of the methods of FIGS. 2-6. An exemplary system includes a storage device (e.g., device storage 116, network device 126) for storing the data set. The system also includes at least one processor for executing code (e.g., processor 102, processor 102') to perform the steps of the methods depicted in FIGS. 2-6.

Exemplary Analysis
The Data Set

Analysis in accordance with exemplary methods taught herein was performed using information derived from tissue samples from a group of patients who had prostate cancer. In various embodiments, tissue samples may be defined as tissue cultures and include in vivo samples. Multiple fields of view (FOVs) were evaluated for each patent.

Other embodiments of the invention may involve tissue samples from a group of patients that share a different commonality or in which only some of the patients share the commonality. For example, one embodiment may involve tissue samples taken from a group of patients to determine if they have another form of cancer, such as breast cancer. Another embodiment may involve tissue samples taken from a group of patients to determine if they have another disease, such as Parkinson's disease. Similarly, other embodiments of the invention may involve larger or smaller groups of patients.

The tissue samples were processed using fluorescence-based multiplexed immunohistochemistry. Twelve biomarkers were used in the analysis. Five of the 12 biomarkers were used for segmentation and compartmentalization of individual cells: NaKATPase, PCAD, DAPI, S6, and Keratin. The remaining markers were pmTOR, PI3 Kp110a, BetaCatenin, EGFR, CleavedCaspase3, pGSK3a, and CleavedPARP. All of the biomarkers passed qualitative staining quality checks.

Other embodiments of the invention may involve different biomarkers. Similarly, other embodiments of the invention involve more or fewer biomarkers.

After autofluorescence removal, illumination correction, and cell segmentation, the data included the median intensity for each protein image in the three compartments of each segmented cell in each FOV in all subjects. Cells were quality controlled by applying the following filters:
1. Cell does not overlap the background (edge areas of the image with incomplete marker data due to misregistration)
2. Cell has 2 or fewer segmented nuclei
3. Cell nucleus contains at least 50 pixels
4. Cell cytoplasm contains at least 50 pixels
5. Cell membrane contains at least 50 pixels Other embodiments of the invention involve different quality control features. Similarly, other embodiments of the invention involve more or fewer quality control features.

After imaging, segmentation, and quality control, 1323 fields of view (FOVs) were successfully graded by the team pathologist (QL). In particular, Gleason scores were manually recorded for all fields of view by the team pathologist (QL) on a scale from 0 to 5. A total of 663 FOVs were assigned a Gleason score greater than zero denoting the presence of cancer, and a total of 660 FOVs were assigned the grade zero. The FOV-level assessment of cancerous or normal was included in the stored meta-information.

Other embodiments may involve different FOV-level assessments, which may be appropriate to the disease or condition affecting at least some of the relevant group of patients. FOV-level assessments of patients with other types of cancer may involve assessments of other types of tumors having their own relevant tumor grades. Other cancer grading systems include, for example, the Bloom-Richardson system for breast cancer and the Fuhrman system for kidney cancer.

The data available for the exemplary analysis also included follow-up information regarding the patients from which the tissue samples were taken. The patient-level assessment of status at five years after the sample was taken (either alive or dead from prostate cancer) was included in the stored meta-information. For the data used in this exemplary analysis, 13 patients had died of prostate cancer within five years and 32 patient were alive after five years.

Exemplary FOV-Level Correlation Between Assessment and Positive Cell Percentages The first example analysis, which correlates FOV-level assessments with FOV-level positive cell percentages, is an example embodiment of method 210 depicted in FIG. 2 performed for multiple different biomarkers. The normalization described below is an example embodiment of the normalization depicted in FIG. 3.

Figure 7:
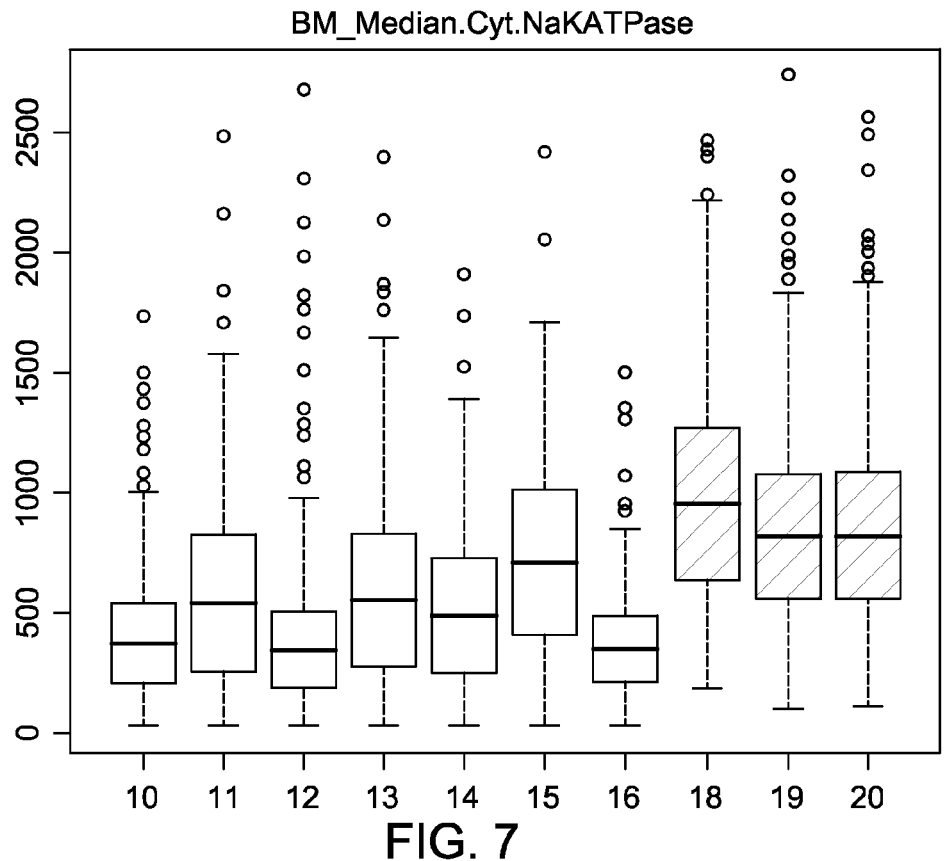
FIG. 7 is a graph of measured intensity values for the expression of biomarker NaKATPase in the cytoplasm of cells in a plurality of FOVs grouped by FOV.
Figure 8:
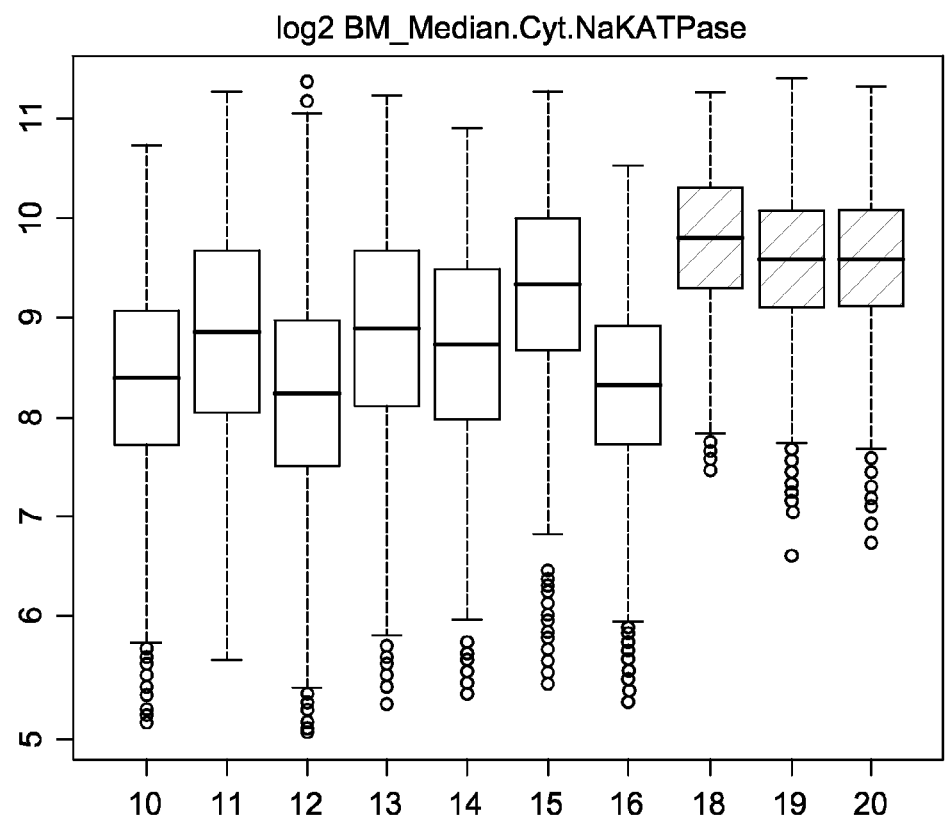
FIG. 8 is a graph of a logarithm base 2 of the intensity values shown in FIG. 6.
Figure 9:
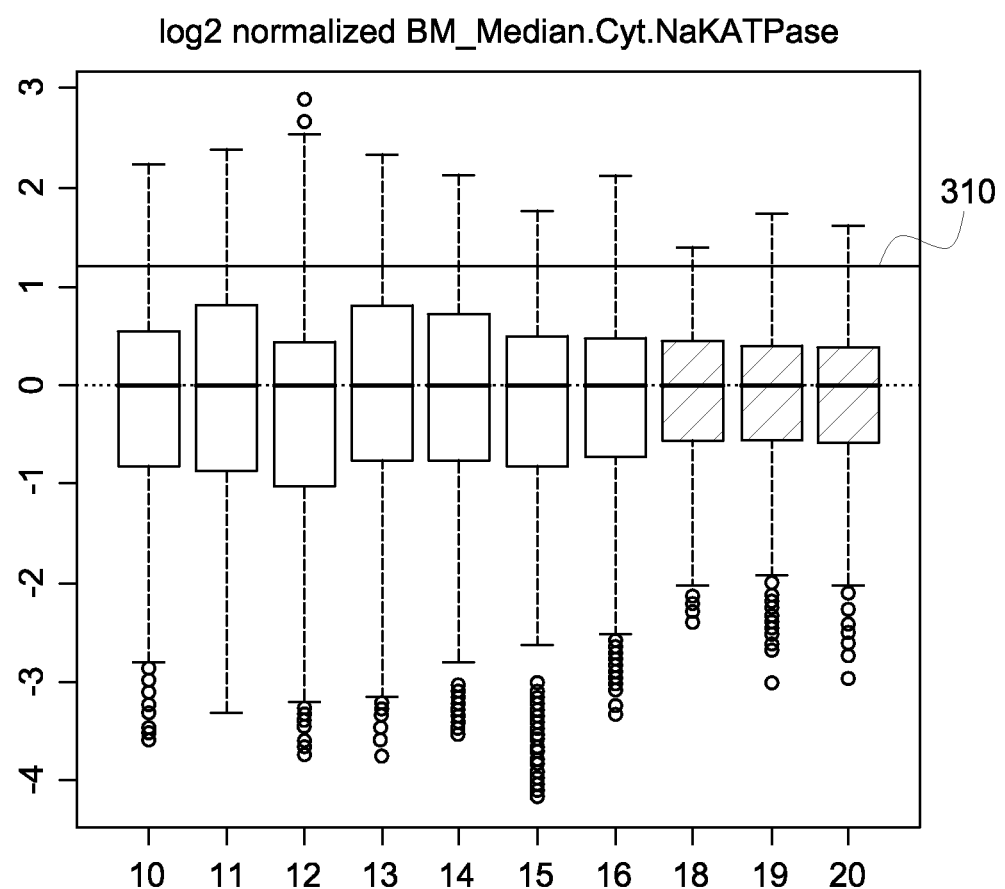
FIG. 9 is a graph of the log base 2 of the intensity values with the distribution for each FOV shifted such that all FOVs have the same median value.

FIGS. 7-9 graphically depict normalization performed on measured intensity data for expression of biomarker NaKAT-Pase in the cytoplasm of cells. FIG. 7 shows the measured expression intensity data for cells, grouped by FOV along the horizontal axis. For illustrative purposes, data for only 10 FOVs out of the 1323 FOVs is shown. For each FOV, the center line of the box plot indicates the median value for the FOV. The box extends from the $25^{th}$ percentile to the $75^{th}$ percentile data showing the variance for each FOV. The dotted lines extend to the bars showing the 2× interquantile for each FOV. In the box plots, the color of the box indicates the assessment of the FOV; a dark box indicates a Gleason score of zero (normal, non-cancerous) and a light box corresponds to a Gleason score greater than zero (cancerous).

FIG. 8 shows a logarithm base 2 of the measured expression intensity data depicted in FIG. 7. As shown in FIG. 8, the median for each FOV is at a different numerical value.

FIG. 9 shows the normalized expression intensity data after the distribution of data for each FOV is shifted such that the median value for each FOV is the same value. Thus, FIG. 9 shows distributions of normalized expression values for different fields of view. In this example, the distributions are shifted such that the median for every distribution is zero.

The line 310 in FIG. 9 illustrates an example normalized expression cutoff that defines 20% of all cells across distributions of normalized expression values for FOVs as positive for the biomarker (or defines 80% of all cells across all FOVs as negative for the biomarker). As noted above, for illustrative purposes, FIG. 9 only shows distributions of normalized expression values for 10 of the 1323 FOVs on which the normalized expression cutoff is based. For FIG. 8, the 20% positive cutoff corresponds to a threshold value of about 1.2, meaning that any cells having a normalized expression value for NaKATPase in the cytoplasm of greater than 1.2 will be labeled positive.

Threshold values were calculated for 5 different cutoffs: 20%, 15%, 10%, 5% and 1% positive cells across all FOVs. In other embodiments, more or fewer cutoffs may be used and the range of the cutoffs used may differ. The number of cutoffs and the range of the cutoffs may vary by cell feature, by biomarker, or both.

Each threshold value was applied to all the different FOVs to determine a percentage of cells in each FOV that exceeded the threshold value, which was termed the "positive cell percentage" for the FOV for that cutoff. A plurality of positive cell percentages were determined for each FOV by applying the plurality of threshold values to the distribution of normalized expression values for the FOV.

In this example, three different cell features (nucleus expression, cytoplasm expression and membrane expression) for twelve different biomarkers were analyzed. For each biomarker, there were 15 different combinations of a cell feature and a normalized expression cutoff. For each biomarker and each cell feature, a plurality of normalized expression cutoffs were applied across all FOVs to produce a plurality of threshold values. Each threshold value was applied to each FOV to determine a positive cell percentage for the FOV associated with the normalized expression cutoff. For each biomarker and each cell feature, the process yields a plurality of cell percentages for each FOV.

After determining the plurality of cell percentages for each cell feature, the cell percentages for each threshold value were correlated with the meta-information for the FOVs. In this example, the meta-information included the assessment of whether a FOV was normal (a Gleason score of zero) or was cancerous (a Gleason grade of greater than zero). A random forest classification model was used to determine the correlation between the positive cell percentages and the meta-information for the FOVs. Examples of Random Forest classification models are described in L. Breiman's "Random Forests" in Machine Learning 45(1), 5-32 (2001).

The random forest classification model was also used to identify which combination of a cell feature and a normalized expression cutoff most closely correlated the positive cell percentages with the meta-information (normal or cancerous) for the biomarker. For each of the 15 combinations of a cell feature and a normalized expression cutoff for a biomarker, the positive cell percentages were input as a predictor into a random forest classification model with the assessments for the FOVs as outcomes. The combination that most accurately predicted the FOV assessments (e.g., had the largest Area Under the Receiver Operating Characteristic Curve—AUC) was identified as the combination that most closely correlated the positive cell percentages with the meta-information. Other performance metrics could have been used to identify the combination that most closely correlated positive cell percentages with the meta-information.

The process was repeated for each of the biomarkers yielding an identified combination of a cell feature and a normalized expression cutoff for each biomarker. The identified combinations are listed in Table 1 below.

TABLE 1

FOV-level Correlation (normal v. cancer)

| Biomarker | Cell Feature (cellular compartment) | Normalized Expression Cutoff (% negative cells) |
| --- | --- | --- |
| NaKATPase | cytoplasm | 85% |
| EGFR | membrane | 95% |
| S6 | cytoplasm | 80% |
| BetaCatenin | cytoplasm | 85% |
| PCAD | cytoplasm | 80% |
| PI3Kp110a | cytoplasm | 85% |
| pmTOR | cytoplasm | 80% |
| Keratin | membrane | 99% |
| DAPI | nucleus | 85% |
| Cleaved PARP | cytoplasm | 80% |
| pGSK3a | cytoplasm | 80% |
| CleavedCaspase3 | cytoplasm | 80% |

Figure 10:
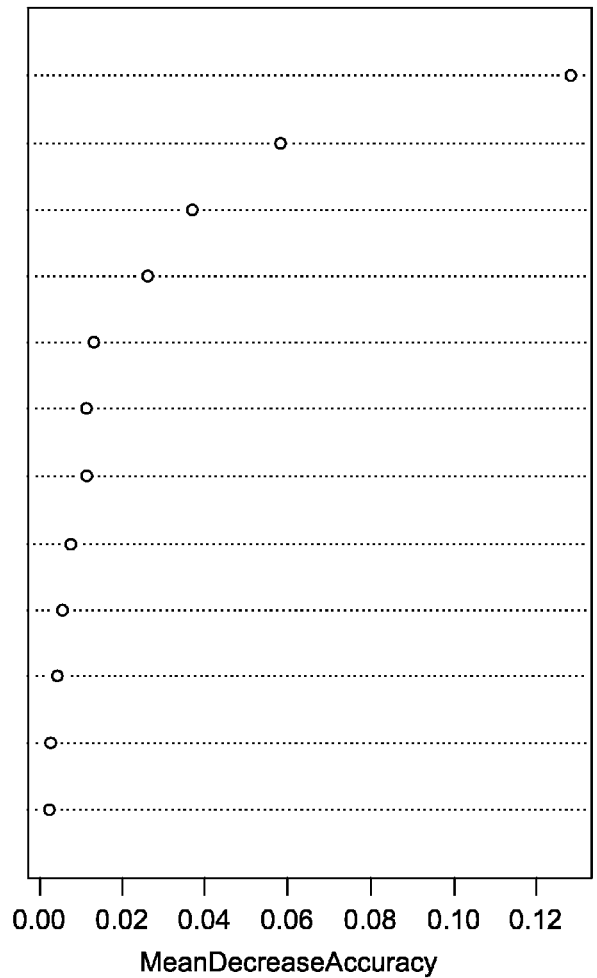
FIG. 10 is a variable importance (mean decrease in accuracy) plot for a random forest model incorporating identified combinations of cell feature-normalized expression cutoff for a plurality of biomarkers to predict FOV-level assessments.

The identified combinations for all the biomarkers were incorporated into a random forest model and the model was probed for the model's partial dependence on each identified combination. FIG. 10 shown a graph of the partial dependence of the model on each of the twelve identified combinations, which are listed on the left. For each identified combination, the horizontal position of the circle indicates how much the accuracy of the model decreased when the model did not take the identified combination into account. For example, omission of the most predictive identified combination from the model, expression of NaKATPase in the cytoplasm at an 85% negative cutoff, decreased the model accuracy by over 12%. The use of "predictive" in the phrase "predictive identified outcome" refers to the accuracy of the identified combination as a predictor of the outcome (assessment) by the random forest classified model, not prediction of a future medical event. Omission of the second most predictive identified combination from the model, expression of EGFR in the membrane at a 95% negative cutoff, decreased the model accuracy by about 6%. Omission of the third most predictive identified combination, expression of S6 in the cytoplasm at an 80% negative cutoff, decreased the model accuracy by over 3%. In contrast, omission of the least predictive identified combination, expression of Cleaved-Caspase3 in the cytoplasm at an 80% negative cutoff, decreased the model accuracy by less than 1%. As shown by the graph, the three most predictive identified combinations are expression of NaKATPase in the cytoplasm with an 85% negative cutoff, expression of EGFR in the membrane with a 95% negative cutoff and expression of S6 in the cytoplasm with an 80% negative cutoff.

FIGS. 11-16 show the relationship between the fraction of positive cells in the FOV and the meta-information for the FOV for the top three predictive identified combinations of cell feature and cutoff. FIG. 11 shows the fraction of positive cells for each FOV for the most predictive identified combination, expression of NaKATPase in the cytoplasm at an 85% negative cutoff. All FOVs assessed as normal (Gleason score of zero) are included in the group on the left and all FOVs assessed as cancerous (Gleason score greater than zero) are included in the group on the right. In the box plots of FIGS. 11, 13 and 15, the height of the rectangular box depicts the variance (25% to 75% of all values), the dark horizontal line in the rectangular box is the median and the dotted lines extend out to upper and lower bars showing the 2× interquantile.

As shown in FIG. 11, with respect to expression of NaKATPase in the cytoplasm at an 85% negative cutoff, the variance in the measurements for the normal group does not the overlap the variance in the measurements for the cancer group, indicating that the percentage of positive cells per FOV correlates strongly with the assessment of cancerous or normal for this identified combination of cell feature and normalized expression cutoff. FIG. 12 shows a logarithm of the odds of a FOV being normal as a function of the fraction of positive cells in the FOV for expression of NaKATPase in the cytoplasm at an 85% negative cutoff.

FIGS. 13 and 14 show the correlation between the second most predictive identified combination, expression of EGFR in the membrane at a 95% negative cutoff, and whether a FOV is assessed as normal or cancerous. In FIG. 13, although the median values for the normal group and the cancer group are not the same, the variances of the two groups overlap showing a weaker correlation with the assessment (normal or cancer) than that shown in FIG. 11. FIG. 14, based on the data of FIG. 13, shows a logarithm of the odds of a FOV being normal as a function of the fraction of positive cells in the FOV for expression of EGFR in the membrane at a 95% negative cutoff.

FIGS. 15 and 16 show the correlation between the third most predictive identified combination, expression of S6 in the cytoplasm at an 80% negative cutoff, and whether a FOV is assessed as normal or cancerous. In FIG. 15, although the median values for the normal group and the cancer group are not the same, the variances of the two groups overlap showing a weaker correlation with the assessment than that shown in FIG. 11. FIG. 16 shows a logarithm of the odds of a FOV being normal as a function of the fraction of positive cells in the FOV for expression of S6 in the cytoplasm at an 80% negative cutoff.

Figure 18:
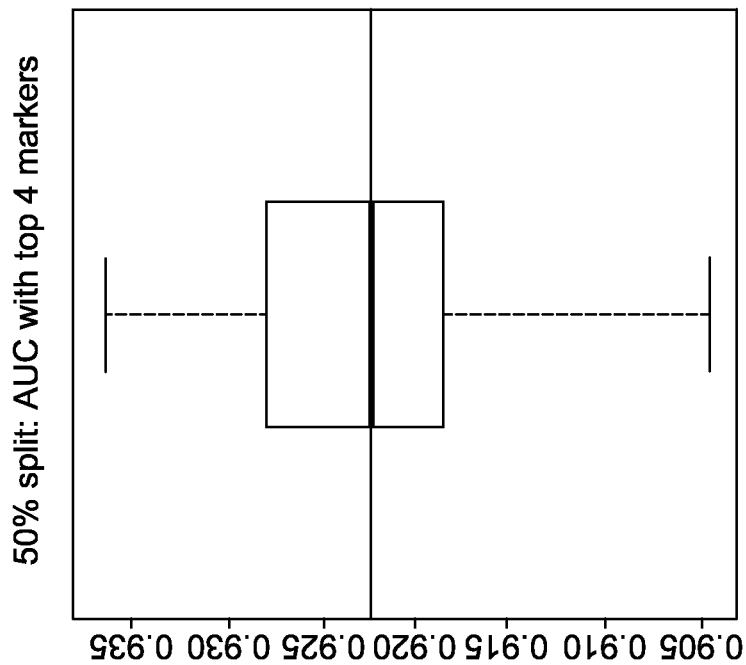
FIG. 18 is a graph of the Area Under the ROC Curve (AUC) statistics for 50% splits.
Figure 17:
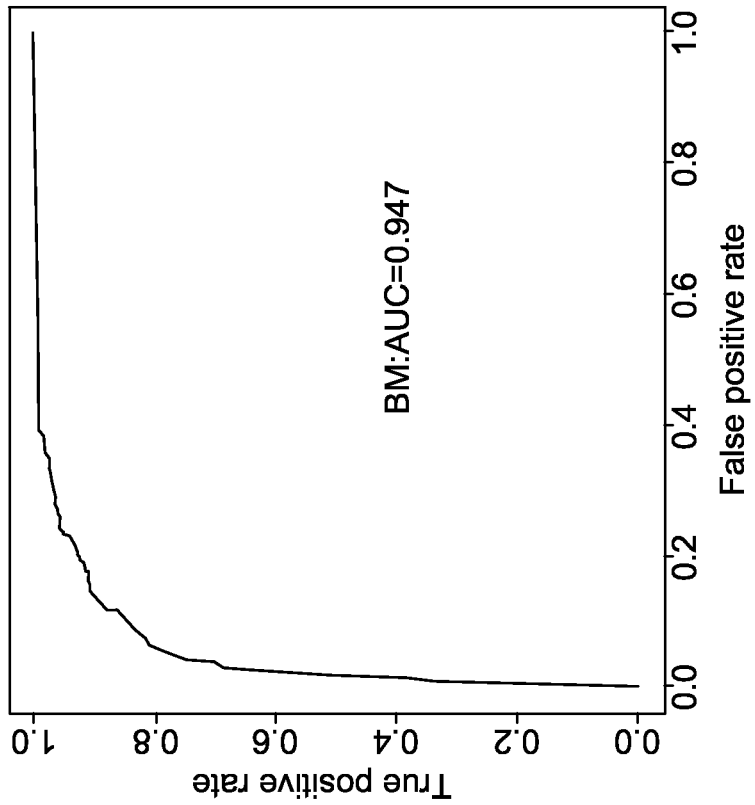
FIG. 17 is a Receiver Operating Characteristic (ROC) curve for a random forest model incorporating the four most predictive cell feature-normalized expression cutoff combinations from FIG. 9.

FIG. 17 is a Receiver Operating Characteristic (ROC) curve for a model incorporating the four most predictive identified cell feature/normalized expression cutoff combinations. The ROC curve shows the true positive rate versus the false positive rate for prediction of whether a FOV is cancerous based on the four positive cell percentages for the FOV. A metric for evaluating the accuracy of a model is the Area Under the ROC Curve (AUC). The AUC for the ROC in FIG. 17 is 0.947. To verify the performance of the model, the model was trained with half the data and tested with half the data repeatedly using different groupings of the data in a process called a 50% split. The AUCs estimated from the 50% splits are plotted in FIG. 18.

Exemplary Patient-Level Correlation Between Assessment and Positive Cell Percentages The second example analysis described below, which correlates patient-level assessments with patient-level positive cell percentages, is an example embodiment of method 250 depicted in FIG. 5 performed for multiple different biomarkers.

In this second example analysis, positive cell percentages were determined for each patient, and the positive cell percentages were correlated with patient-level assessments, namely the patient's five year survival status. The dataset included 32 patients that were alive at five years after the tissue sample was taken (alive) and 12 patients that died from prostate cancer within five years of the tissue sample being taken (dead). Patients who dies of causes other than prostate cancer within five years of the sample being taken were excluded from this second analysis.

In the second example analysis, the same twelve biomarkers, the same three cell features (nucleus expression, cytoplasm expression and membrane expression) and the same five normalized expression cutoffs (80%, 85%, 90%, 95%, and 99% negative) were used. For each biomarker, there were 15 different combinations of a cell feature and a normalized expression cutoff. The same normalization of the biomarker expression intensity data as described above for the first example analysis was performed for all FOVs.

Similar to the first example analysis, for each cell feature, a plurality of normalized expression cutoffs were applied across all FOVs to determine a determine a plurality of threshold values. However, in this example analysis, the threshold value of the cutoff was applied across all FOVs from the same patient to determine a positive cell percentage for the patient. The corresponding positive cell percentage for the patient is the total number of cells above the threshold value for all the FOVs for the patient divided by the total number of cells in all the FOVs for the patient. In this second example analysis, for each cell feature, a plurality of positive cell percentages were determined for each patient.

After determining the plurality of cell percentages for each patient for the feature, the cell percentages for each threshold value for the feature were correlated with the meta-information for the patients. In this example, the meta-information included the patient's five year survival status, namely whether the patient died of prostate cancer within five years or did not. A random forest classification model was used to determine the correlation between the positive cell percentages and the meta-information across all patients. The random forest classification model was also used to identify a combination of cell feature a normalized expression cutoff that most closely correlated the positive cell percentages with the five year survival status across the patients by identifying the combination that produced predictors (positive cell percentages) that most accurately predicted outcome (survival status of patients). The prediction accuracy was measured by a performance parameter (e.g., AUC).

The process was repeated for all 12 biomarker producing an identified combination of a cell feature and a cutoff for each biomarker. The identified combinations are listed in Table 1 below as well as other predictors that can be incorporated into a model, such as age of the patient and Gleason score for the patient's cancer.

TABLE 2

| Patient-Level Correlation (5 year survival) | | |
|---|---|---|
| Predictors | Cell Feature (cellular compartment) | Normalized Expression Cutoff (% negative cells) |
| S6 | cytoplasm | 90% |
| NaKATPase | cytoplasm | 90% |
| Age | | |
| Keratin | cytoplasm | 99% |
| PCAD | cytoplasm | 90% |
| Beta Catenin | cytoplasm | 90% |
| PI3Kp110a | cytoplasm | 85% |

TABLE 2-continued

Patient-Level Correlation (5 year survival)

| Predictors | Cell Feature (cellular compartment) | Normalized Expression Cutoff (% negative cells) |
|---|---|---|
| Gleason Score | | |
| Cleaved PARP | nucleus | 99% |
| DAPI | cytoplasm | 90% |
| pmTOR | cytoplasm | 99% |
| pGSK3a | nucleus | 90% |
| Cleaved Caspase3 | membrane | 90% |
| EGFR | membrane | 95% |

Figure 19:
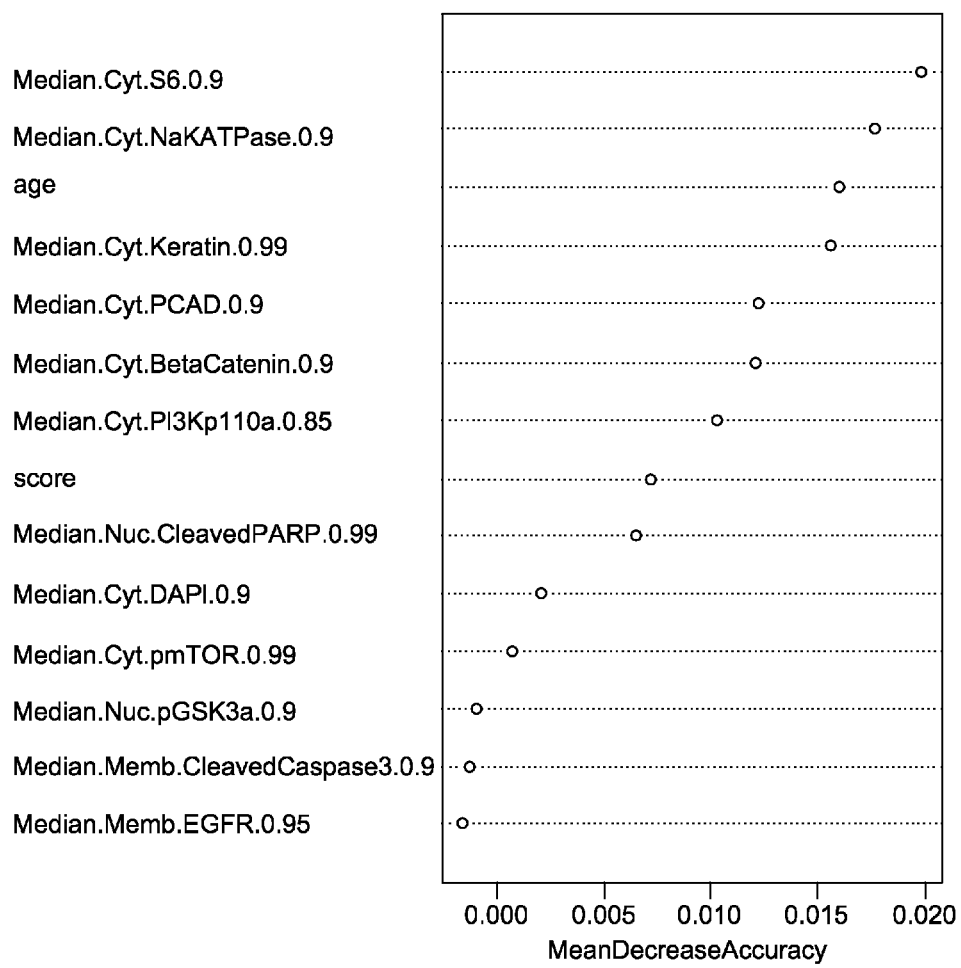
FIG. 19 is a variable importance (mean decrease in accuracy) plot for a random forest model incorporating identified combinations of cell feature-normalized expression cutoff for a plurality of biomarkers to predict patient-level assessments.

The identified combinations for each biomarker, the age of the patient and the Gleason score of the patient's cancer were incorporated into a random forest model and the model was probed for the model's partial dependence on each predictor (the twelve identified combinations, the age and the Gleason score). FIG. 19 shown a graph of the partial dependence of the model on the predictors, which are listed on the left. For each predictor, the horizontal position of the circle indicates how much the accuracy of the model decreased when the model did not take the predictor into account. For example, omission of the most predictive identified combination from the model, expression of S6 in the cytoplasm at a 90% negative cutoff, decreased the model accuracy by about 2%. Omission of the second most predictive identified combination from the model, expression of NaKATPase in the cytoplasm at a 90% negative cutoff, decreases the model accuracy by about 1.7%. Omission of the third most significant predictor, age, decreases the model accuracy by about 1.6%. In contrast, omission of the least predictive identified combination, expression of EGFR expressed in the membrane at a 95% negative cutoff, actually increases the model's accuracy.

FIGS. 20-25 show the relationship between the fraction of positive cells for the patient and the meta-information for the patient for the top three combinations. In the box plots of FIGS. 20, 21 and 22, the height of the rectangular box depicts the variance (25% to 75% of all values), the dark horizontal line in the rectangular box is the median and the dotted lines extending out to upper and lower bars show the 2x interquantile. For FIGS. 20, 21 and 22, all patients that survived five years (alive) are included in a group on the left and all patients that did not (dead) are included in a group on the right.

FIGS. 20 and 21 show the correlation between positive cell percentages and five year survival status for the most predictive identified combination. FIG. 20 graphs the fraction of positive cells for each patient for expression of S6 in the cytoplasm at a 90% negative cutoff, with the patients grouped by those that survived five years, and those that did not. FIG. 21 shows a logarithm of the odds of five year survival (alive) as a function of the fraction of positive cells for the patient for expression of S6 in the cytoplasm at a 90% negative cutoff.

FIGS. 22 and 23 show the correlation between positive cell percentages and five year survival status for the second most predictive identified combination. FIG. 22 graphs the fraction of positive cells for expression of NaKATPase in the cytoplasm at a 90% negative cutoff, with the patients grouped by those that survived five years, and those that did not. FIG. 23, shows a logarithm of the odds of five year survival (alive) as a function of the fraction of positive cells for the patient for expression of NaKATPase in the cytoplasm at a 90% negative cutoff.

FIGS. 24 and 25 show the correlation between positive cell percentages and five year survival status for the third most predictive identified combination. FIG. 24 graphs the fraction of positive cells for each patient for expression of Keratin in the cytoplasm at a 99% negative cutoff, with the patients grouped by those that survived five years, and those that did not. FIG. 25, shows a logarithm of the odds of five year survival (alive) as a function of the fraction of positive cells for the patient for expression of Keratin in the cytoplasm at a 99% negative cutoff.

Figure 27:
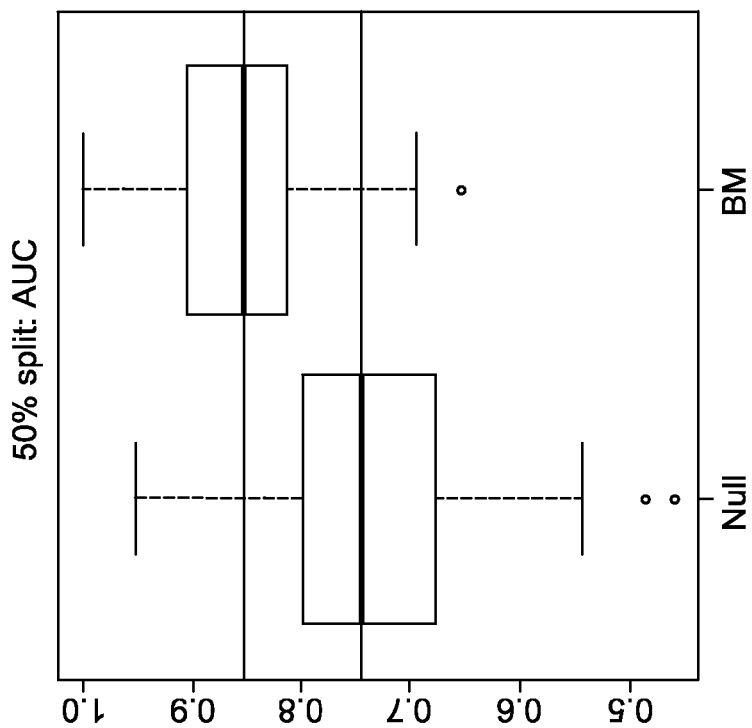
FIG. 27 is a graph of the Area Under the ROC Curve (AUC) statistics for 50% splits for the BM model and the Null model.
Figure 26:
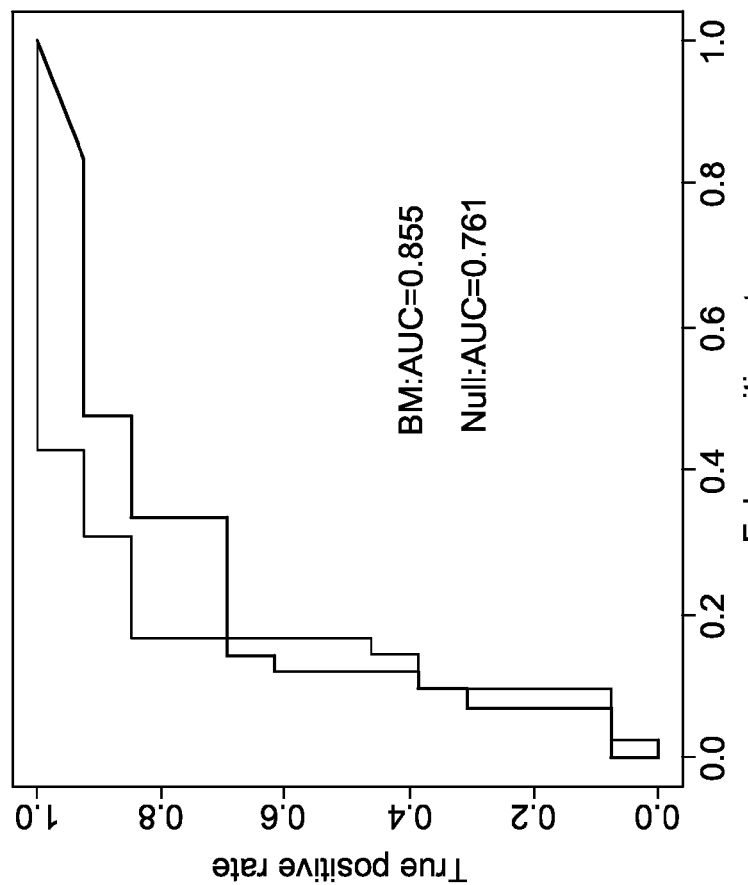
FIG. 26 is a ROC curve for a model (BM) incorporating age, Gleason score and the two most predictive combinations from FIG. 18 compared with a model (Null) incorporating only age and Gleason score.

FIG. 26 is a Receiver Operating Characteristic (ROC) curve for a model (labeled the BM model) incorporating the two most predictive identified cell feature/normalized expression cutoff combinations, the age of the patient and the Gleason score of the patient's cancer. The BM model is compared with a model (labeled the Null model) that only incorporates the patient's age and the Gleason score of the patient's cancer. The BM model with an AUC of 0.855 outperformed the Null model, which had an AUC of 0.761. FIG. 27 compares the 50% split AUC statistics for the BM model and the Null model.

While some features of embodiments of the invention have been illustrated and described herein, many modifications and changes will be clear to those of skill in the art based on this application. It is, therefore, to be understood that the appended claims are intended to cover all such modifications and changes as fall within the true spirit of the invention.

Although the claims recite specific combinations of limitations, the invention expressly encompasses each independent claim by itself and also in conjunction with any possible combination of limitations articulated in the related dependent claims except those that are clearly incompatible.

The invention claimed is:

1. A computer-implemented method of analyzing tissue features based on multiplexed biometric images, the method comprising:
storing in a computer-readable medium a data set comprising cell profile data for a biomarker with respect to a plurality of fields of view and an association of the cell profile data with meta-information including an assessment for each field of view, the cell profile data including biomarker expression intensity data for a plurality of cell features in a field of view, the biomarker expression intensity data obtained from multiplexed biometric images capturing the expression of the biomarker with respect to a field of view in which individual cells are delineated and segmenting into compartments;
normalizing the biomarker expression intensity data for a first cell feature in the plurality of cell features across the plurality of fields of view to obtain a distribution of normalized expression values for the first cell feature for each field of view and where normalizing comprises;
taking a logarithm of the biomarker expression intensity data for the first cell feature for each field of view to obtain a distribution of log biomarker expression intensity data for the first cell feature for each field of view; and
shifting the distribution of log biomarker intensity expression data for the first cell feature for each field of view such that a median of each distribution is at the same numerical value for all fields of view to produce a distribution of normalized expression values for the first cell feature for each field of view;
calculating a plurality of threshold values for the first cell feature from a plurality of normalized expression cutoffs applied to the distributions of normalized expression values for all fields of view wherein the threshold values are from 80-99% and determined from a random forest classification model;

determining a plurality of positive cell percentages for the first cell feature for each field of view, wherein each positive cell percentage in the plurality of positive cell percentages corresponds to a threshold value applied to the distribution of normalized expression values for the first cell feature for the field of view;
correlating the positive cell percentages for each threshold value for the first cell feature with the meta-information for the fields of view;
repeating the normalizing, calculating, determining, and correlating steps for a second cell feature;
identifying a combination of one of the plurality of cell features and one of the plurality of normalized expression cutoffs that most closely correlates the positive cell percentages with the meta-information for the fields of view; and
defining the percentage of positive cells.

2. The method of claim 1, further comprising repeating the normalizing, calculating, determining and correlating steps for a third cell feature before identifying a combination of one of the plurality of cell features and one of the plurality of normalized expression cutoffs that most closely correlates the positive cell percentages with the meta-information for the fields of view.

3. The method of claim 1, wherein the plurality of cell features comprises a cell compartment-level expression intensity of the biomarker for a plurality of different types of cell compartments.

4. The method of claim 1, wherein the plurality of cell features is selected from a group consisting of: a median biomarker expression intensity of the whole cell, a nucleus biomarker expression intensity, a membrane biomarker expression intensity, and a cytoplasm biomarker expression intensity.

5. The method of claim 1, wherein the meta-information including an assessment for each field of view comprises a designated tissue grade for the field of view.

6. The method of claim 1, wherein the meta-information including an assessment for each field of view comprises a diagnosis or a prognosis for the field of view.

7. The method of claim 1, further comprising creating cell profile data.

8. The method of claim 1 further comprising obtaining images of a tissue sample of a patient from which multiplexed biometric images are produced.

9. The method of claim 1, further comprising delineating individual cells and segmenting the cells into compartments in a field of view of an image of a tissue sample for a plurality of images of tissue samples to produce the multiplexed biometric images.

10. A computer-implemented method of analyzing tissue features based on multiplexed biometric images comprising:
storing in a computer-readable medium a data set comprising cell profile data for a plurality of biomarkers with respect to a plurality of fields of view and an association of the cell profile data with meta-information including an assessment for each field of view, the cell profile data including biomarker expression intensity data for a plurality of cell features in a field of view, the biomarker expression intensity data obtained from multiplexed biometric images capturing the expression of the plurality of biomarkers with respect to a field of view in which individual cells are delineated and segmenting into compartments;
normalizing the biomarker expression intensity data for a first cell feature and a first biomarker in the plurality of biomarkers across the plurality of fields of view to obtain a distribution of normalized expression values for the first cell feature for each field of view where normalizing comprises;
taking a logarithm of the biomarker expression intensity data for the first cell feature for each field of view to obtain a distribution of log biomarker expression intensity data for the first cell feature for each field of view; and
shifting the distribution of log biomarker intensity expression data for the first cell feature for each field of view such that a median of each distribution is at the same numerical value for all fields of view to produce a distribution of normalized expression values for the first cell feature for each field of view
calculating a plurality of threshold values for the first cell feature from a plurality of normalized expression cutoffs applied to the distributions of normalized expression values for all fields of view wherein the threshold values are from 80-99% and determined from a random forest classification model;
determining a plurality of positive cell percentages for the first cell feature and the first biomarker for each field of view, wherein each positive cell percentage in the plurality of positive cell percentages corresponds to a threshold value applied to the distribution of normalized expression values for the first cell feature for the field of view;
correlating the positive cell percentages for each threshold value for the first cell feature and the first biomarker with the meta-information across for fields of view;
repeating the normalizing, calculating, determining, and correlating steps for a first cell feature of a second biomarker; and
identifying a combination of a cell feature of one of the plurality of biomarkers and one of the plurality of normalized expression cutoffs that most closely correlates the positive cell percentages with the meta-information for the fields of view; and
defining the percentage of positive cells.

11. The method of claim 10, further comprising repeating the normalizing, calculating, determining and correlating steps for a second cell feature before identifying a combination of a cell feature of one of the plurality of biomarkers and one of the plurality of normalized expression cutoffs that most closely correlates the positive cell percentages with the meta-information for the fields of view.

12. The method of claim 10, further comprising, for each biomarker, repeating the normalizing, identifying, determining and correlating steps for a third cell feature before identifying a combination of a cell feature of one of the plurality of biomarkers and one of the plurality of normalized expression cutoffs that most closely correlates the positive cell percentages with the meta-information for the fields of view.

13. A computer-implemented method of analyzing tissue features based on multiplexed biometric images comprising:
storing in a computer-readable medium a data set comprising cell profile data for a biomarker with respect to a plurality of fields of view, the cell profile data including biomarker expression intensity data for a plurality of cell features in a field of view, the biomarker expression intensity data obtained from multiplexed biometric images from a plurality of patients, the multiplexed biometric images capturing the expression of the biomarker with respect to a field of view in which individual cells are delineated and segmenting into compartments, the data set further comprising an association of the cell profile data with meta-information including an assessment for each patient;

normalizing the biomarker expression intensity data for a first cell feature in the plurality of cell features across the plurality of fields of view to obtain a distribution of normalized expression values for the first cell feature for each field of view where normalizing comprises;

taking a logarithm of the biomarker expression intensity data for the first cell feature for each field of view to obtain a distribution of log biomarker expression intensity data for the first cell feature for each field of view; and shifting the distribution of log biomarker intensity expression data for the first cell feature for each field of view such that a median of each distribution is at the same numerical value for all fields of view to produce a distribution of normalized expression values for the first cell feature for each field of view;

calculating a plurality of threshold values for the first cell feature from a plurality of normalized expression cutoffs applied to the distributions of normalized expression values for all fields of view wherein the threshold values are from 80-99% and determined from a random forest classification model;

determining a plurality of positive cell percentages for the first cell feature for each patient, wherein each positive cell percentage in the plurality of cell percentages corresponds to a threshold value applied to distributions of normalized expression values for the first cell feature for all of fields of view associated with the patient;

correlating the positive cell percentages for each threshold value for the first cell feature with the meta-information for the patients;

repeating the normalizing, calculating, determining, and correlating steps for a second cell feature;

identifying a combination of one the plurality of cell features and one of the plurality of normalized expression cutoffs that most closely correlates the positive cell percentages with the meta-information for the patients; and defining the percentage of positive cells.

14. The method of claim 13, further comprising repeating the normalizing, calculating, determining, and correlating steps for a third cell feature before identifying a combination of one the plurality of cell features and one of the plurality of normalized expression cutoffs that most closely correlates the positive cell percentages with the meta-information for the patients.

15. The method of claim 13, wherein the plurality of cell features comprises a cell compartment-level expression intensity of the biomarker for a plurality of different types of cell compartments.

16. The method of claim 13, wherein the plurality of cell features is selected from a group consisting of: a median biomarker expression intensity of the whole cell, a nucleus biomarker expression intensity, a membrane biomarker expression intensity, and a cytoplasm biomarker expression intensity.

17. The method of claim 13, wherein the meta-information including an assessment for each patient comprises a diagnosis or a prognosis for the patient.

18. The method of claim 13, wherein the meta-information including an assessment for each patient comprises a survival time for the patient.

19. The method of claim 13, further comprising creating cell profile data.

20. The method of claim 13, further comprising obtaining images of a tissue sample of a patient from which multiplexed biometric images are produced.

21. The method of claim 13, further comprising delineating individual cells and segmenting the cells into compartments in a field of view of an image of a tissue sample for a plurality of images of tissue samples to produce the multiplexed biometric images.

22. A system for analyzing tissue features based on multiplexed biometric image data comprising:

a storage device for storing a data set comprising cell profile data for a biomarker with respect to a plurality of fields of view and an association of the cell profile data with meta-information including an assessment for each field of view, the cell profile data including biomarker expression intensity data for a plurality of cell features in a field of view, the biomarker expression intensity data obtained from multiplexed biometric images capturing the expression of the biomarker with respect to a field of view in which individual cells are delineated and segmenting into compartments; and at least one processor for executing code that causes the at least one processor to perform, the steps of:

normalizing the biomarker expression intensity data for a first cell feature in the plurality of cell features across the plurality of fields of view to obtain a distribution of normalized expression values for the first cell feature for each field of view where normalizing comprises;

taking a logarithm of the biomarker expression intensity data for the first cell feature for each field of view to obtain a distribution of log biomarker expression intensity data for the first cell feature for each field of view; and shifting the distribution of log biomarker intensity expression data for the first cell feature for each field of view such that a median of each distribution is at the same numerical value for all fields of view to produce a distribution of normalized expression values for the first cell feature for each field of view;

calculating a plurality of threshold values for the first cell feature from a plurality of normalized expression cutoffs applied to the distributions of normalized expression values for all fields of view wherein the threshold values are from 80-99% and determined from a random forest classification model;

determining a plurality of positive cell percentages for the first cell feature for each field of view, wherein each positive cell percentage in the plurality of positive cell percentages corresponds to a threshold value applied to the distribution of normalized expression values for the first cell feature for the field of view;

correlating the positive cell percentages for each threshold value for the first cell feature with the meta-information for the fields of view;

repeating the normalizing, calculating, determining, and correlating steps for a second cell feature;

identifying a combination of one of the plurality of cell features and one of the plurality of normalized expression cutoffs that most closely correlates the positive cell percentages with the meta-information for the fields of view; and defining the percentage of positive cells.

23. The system of claim 22, wherein the least one processor executes code that causes the at least one processor to perform, steps further comprising the step of repeating the normalizing, calculating, determining, and correlating steps for a third cell feature before identifying a combination of one of the plurality of cell features and one of the plurality of normalized expression cutoffs that most closely correlates the positive cell percentages with the meta-information for the fields of view.

24. The system of claim 22, wherein the plurality of cell features comprises a cell compartment-level expression of the biomarker for a plurality of different types of cell compartments.

25. The system of claim 22, wherein the meta-information including an assessment for each field of view comprises a designated tissue grade for the field of view.

26. The system of claim 22, wherein the meta-information including an assessment for each field of view comprises a diagnosis or a prognosis for the field of view.

27. A system for analyzing tissue features based on multiplexed biometric image data comprising:
a storage device for storing a data set comprising cell profile data for a biomarker with respect to a plurality of fields of view, the cell profile data including biomarker expression intensity data for a plurality of cell features in a field of view, the biomarker expression intensity data obtained from multiplexed biometric images from a plurality of patients, the multiplexed biometric images capturing the expression of the biomarker with respect to a field of view in which individual cells are delineated and segmenting into compartments, the data set further comprising an association of the cell profile data with meta-information including an assessment for each patient; and
at least one processor for executing code that causes the at least one processor to perform, the steps of:
normalizing the biomarker expression intensity data for a first cell feature in the plurality of cell features across the plurality of fields of view to obtain a distribution of normalized expression values for the first cell feature for each field of view where normalizing comprises;
taking a logarithm of the biomarker expression intensity data for the first cell feature for each field of view to obtain a distribution of log biomarker expression intensity data for the first cell feature for each field of view; and
shifting the distribution of log biomarker intensity expression data for the first cell feature for each field of view such that a median of each distribution is at the same numerical value for all fields of view to produce a distribution of normalized expression values for the first cell feature for each field of view;
calculating a plurality of threshold values for the first cell feature from a plurality of normalized expression cutoffs applied to the distributions of normalized expression values for all fields of view wherein the threshold values are from 80-99% and determined from a random forest classification model;
determining a plurality of positive cell percentages for the first cell feature for each patient, wherein each positive cell percentage in the plurality of cell percentages corresponds to a threshold value applied to distributions of normalized expression values for the first cell feature for all of fields of view associated with the patient;
correlating the positive percentages for each threshold value for the first feature with the meta-information for the patients;
repeating the normalizing, calculating, determining, and correlating steps for a second cell feature;
identifying a combination of one the plurality of cell features and one of the plurality of normalized expression cutoffs that most closely correlates the positive cell percentages with the meta-information for the patients and
defining the percentage of positive cells.

28. The system of claim 27, wherein the least one processor executes code that causes the at least one processor to perform, steps further comprising the step of repeating the normalizing, calculating, determining, and correlating steps for a third cell feature before identifying a combination of one the plurality of cell features and one of the plurality of normalized expression cutoffs that most closely correlates the positive cell percentages with the meta-information for the patients.

29. The system of claim 27, wherein the plurality of cell features comprises a cell compartment-level expression intensity of the biomarker for a plurality of different types of cell compartments.

30. The system of claim 27, wherein the meta-information including an assessment for each patient comprises a diagnosis or a prognosis for the patient.

31. The system of claim 27, wherein the meta-information including an assessment for each patient comprises a survival time for the patient.

* * * * *